United States Patent
Unamunzaga Escosura et al.

(10) Patent No.: US 11,473,065 B2
(45) Date of Patent: Oct. 18, 2022

(54) **METHOD FOR OBTAINING A BIOMASS OF A MICROALGA OF THE SPECIES *TETRASELMIS CHUII* ENRICHED IN SUPEROXIDE DISMUTASE (SOD)**

(71) Applicant: FITOPLANCTON MARINO, S.L., El Puerto de Santa Maria (ES)

(72) Inventors: Carlos Unamunzaga Escosura, El Puerto de Santa Maria (ES); Eulalia Mantecón Gálvez, El Puerto de Santa Maria (ES)

(73) Assignee: FITOPLANCTON MARINO, S.L., El Puerto de Santa Maria (ES)

( * ) Notice: Subject to any disclaimer, the term of this patent is extended or adjusted under 35 U.S.C. 154(b) by 0 days.

(21) Appl. No.: 15/571,910

(22) PCT Filed: May 5, 2016

(86) PCT No.: PCT/EP2016/060131
§ 371 (c)(1),
(2) Date: Nov. 6, 2017

(87) PCT Pub. No.: WO2016/177853
PCT Pub. Date: Nov. 10, 2016

(65) Prior Publication Data
US 2018/0119114 A1 May 3, 2018

(30) Foreign Application Priority Data
May 6, 2015 (EP) .................................... 15382235

(51) Int. Cl.
| | | |
|---|---|---|
| *C12N 9/02* | (2006.01) | |
| *C12N 1/12* | (2006.01) | |
| *C12N 9/96* | (2006.01) | |
| *A23L 33/135* | (2016.01) | |
| *A61K 8/9706* | (2017.01) | |
| *A61K 8/66* | (2006.01) | |
| *A61K 36/02* | (2006.01) | |
| *A61K 38/44* | (2006.01) | |
| *A61K 9/00* | (2006.01) | |
| *A61Q 19/00* | (2006.01) | |

(52) U.S. Cl.
CPC .......... *C12N 9/0089* (2013.01); *A23L 33/135* (2016.08); *A61K 8/66* (2013.01); *A61K 8/9706* (2017.08); *A61K 36/02* (2013.01); *A61K 38/446* (2013.01); *A61Q 19/00* (2013.01); *C12N 1/12* (2013.01); *C12N 9/96* (2013.01); *C12Y 115/01001* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 5,179,012 A | 1/1993 | Gudin et al. | |
| 5,464,614 A | 11/1995 | Meyer | |
| 2009/0130139 A1 | 5/2009 | Mekideche | |
| 2011/0045564 A1* | 2/2011 | Dhamwichukorn | ..... C12N 1/06 |
| | | | 435/170 |

FOREIGN PATENT DOCUMENTS

| | | |
|---|---|---|
| EP | 0 599 2 62 A2 | 6/1994 |
| ES | 2 232 450 T3 | 6/2005 |
| FR | 2785909 | 5/2000 |
| FR | 2785910 | 5/2000 |
| JP | H0269181 A * | 3/1990 |
| WO | WO/1998/008584 | 3/1998 |
| WO | 0075282 | 12/2000 |
| WO | WO 0075282 | 12/2000 |
| WO | 08099924 | 8/2008 |
| WO | 10054325 | 5/2010 |

OTHER PUBLICATIONS

Cirulis, J.T. et al. 2013. Management of oxidative stress by microalgae. Canadian Journal of Physiology and Pharmacology 91: 15-21. specif. pp. 15, 16.*
Ahmed, F. et al. 2014. Profiling of carotenoids and antioxidant capacity of microalgae from subtropical coastal and brackish waters. Food Chemistry 165: 300-306. specif. pp. 300, 301, 304.*
Bafana, A. et al. 2011. Superoxide dismutase: an industrial perspective. Critical Reviews in Biotechnology 31(1): 65-76. specif. pp. 66, 67, 68, 69.*
Veldhuis, M.J.W. et al. 1987. Influence of phosphate depletion on the growth and colony formation of Phaeocystis pouchetti. Marine Biology 95: 47-54. specif. pp. 47, 48.*
Vagenende, V. et al. 2009. Mechanisms of protein stabilization and prevention of protein aggregation by glycerol. Biochemistry 48: 11084-11096. specif. p. 11084.*
English MT. Matsunaga, T. et al. Production of superoxide dismutase. Japanese Patent Application Publication No. JPH0269181(A); Date of Publication Mar. 8, 1990. Specification pp. 1-5. specif. pp. 1, 2, 3, 4.*
Marine Phytoplankton 5000. Dec. 16, 2014 Press release. From fish food to superfood: Marine phytoplankton 500 gives consumers powerful defense against ravages of oxidative stress. Downloaded from the internet on Nov. 7, 2019, pp. 1-3. specif. p. 1.*
Cont. Marine Phytoplankton 5000. Dec. 16, 2014 Press release. Downloaded at https://www.prnewswire.com/news-releases/from-fish-food-to-superfood-marine-phytoplankton-5000-gives-consumers-powerful-defense-against-ravages-of-oxidative-stress-300010193.html.*

(Continued)

*Primary Examiner* — Olivia M. Wise
*Assistant Examiner* — Sharon M. Papciak
(74) *Attorney, Agent, or Firm* — Gary J. Gershik

(57) ABSTRACT

The invention relates to a method for enriching a biomass of a microalga of the species *Tetraselmis chuii* in superoxide dismutase (SOD) by placing said microalga under abiotic stress conditions. The invention also relates to a biomass enriched in SOD as well as to an extract of the microalga and to the uses thereof as a pharmaceutical composition, as a cosmetic or in foodstuff.

13 Claims, 14 Drawing Sheets

(56) References Cited

OTHER PUBLICATIONS

Marine Phytoplankton 5000 website product sale. Nov. 30, 2014. TetraSOD-80g Marine Phytoplankton 5000 pure powder plankton. Downloaded from the internet on Nov. 6, 2019. pp. 1-3. specif. pp. 1, 2, 3.*
Cont. Marine Phytoplankton 5000 website product sale. Nov. 30, 2014. Downloaded at http://www.marineplankton5000.com/buy-pure-sod-plankton-5000/80-grams-powder-marine-phytoplankton-5000.html.*
Kumar, K.S. et al. Mar. 2015. Microalgae—a promising tool for heavy metal remediation. Ecotoxicology and Environmental Safety 113: 329-352. specif. pp. 329, 332, 333, 343.*
Okamoto, O.K. et al. 1996. Effects of cadmium on growth and superoxide dismutase activity of the marine microalga *Tetraselmis gracilis* (Prasninophyceae). Journal of Phycology 32: 74-79. specif. pp. 74, 75, 76, 77.*
Yilancioglu, K. et al. Mar. 2014. Oxidative stress is as a mediator for increased lipid accumulation in newly isolated Dunaliella sallina strain. PLoS ONE 9(3); 1-13. specif. pp. 1, 8.*
International Search Report issued by the International Searching Authority (ISA/O.E.P.M.) dated Aug. 3, 2016 in connection with International Application No. PCT/EP2016/060131.
Bottino, N.R. et al., "The Effects of Arsenate and Arsenite on the Growth And Morphology of the Marine Unicellular Algae *Tetraselmis chui* (Chlorophyta) and *Hymenomonas carterae* (Chrysophyta)", Journal of Experimental Marine Biology And Ecology, vol. 33, 1978, pp. 153-168.
Chung, C.-C. et al., "Identification of a High-Affinity Phosphate Transporter Gene in a Prasinophyte Alga, *Tetraselmis chui*, and Its Expression under Nutrient Limitation", Applied And Environmental Microbiology, vol. 69, No. 2, 2003, pp. 754-759.
Custódio, L. et al., "Fatty acid composition and biological activities of Isochrysis galbana T-ISO, *Tetraselmis* sp. And *Scenedesmus* sp.: possible application in the pharmaceutical and functional food industries", Journal of Applied Phycology, vol. 26, No. 1, 2013, pp. 151-161.
Debelius, B. et al., "Toxicity and bioaccumulation of copper and lead in five marine microalgae", Ecotoxicology And Environmental Safety, vol. 72, No. 5, 2009, pp. 1503-1513.
Dickson, D.M.J. et al., "Osmotic Adjustment In Marine Eukaryotic Algae The Role Inorganic Ions Quaternary Ammonium Tertiary Sulfonium And Carbohydrate Solutes II. Prasinophytes And Haptophytes", New Phytologist, vol. 106, No. 4, 1987, pp. 657-666.
Goiris, K. et al, "Antioxidant potential of microalgae in relation to their phenolic and carotenoid content" Journal of Applied Phycology, vol. 24, No. 6, 2012, pp. 1477-1486.
Janknegt, P.J., et al., "Short-term antioxidative responses of 15 microalgae exposed to excessive irradiance including ultraviolet radiation", European Journal of Phycology, vol. 44, No. 4, 2009, pp. 525-539.
Kumar, R.R. et al., "Enzymatic and non-enzymatic antioxidant potentials of Chlorella vulgaris grown in effluent of a confectionery industry", Journal of Food Science and Technology, vol. 51, No. 2, 2011, pp. 322-328.
Marin, N. et al., "Cultivo de Microalgas y el Rotifero Brachionus Plicatilis a Gran Escala [Mass culture of microalgae and rotifer *Brachionus plicatilis*]", ACTA Cientifica Venezolana, vol. 45, No. 3, 1994, pp. 226-230.
Okamoto, O.K., et al., "Effects of Cadmium on Growth And Superoxide Dismutase Activity of the Marine Microalga *Tetraselmis gracilis* (Prasinophyceae)", Journal of Phycology, vol. 32, 1996, pp. 74-79.
Perfeto, P.N.M., et al., "Cultivo unialgal de Tetraselmis chuii Butcher (Prasinophyceae-Pyramimonadales) com fertilizante Agricola em diferentes salinidades. Unialgal culture of Tetraselmis chuii Butcher (Prasinophyceae-Pyramimonadales) with agriculture fertilizer in different salinity", Iheringia/Série Botânica, No. 48, 1997, pp. 3-14.

Saha, S.K., et al., "Effect of macro- and micro-nutrient limitation on superoxide dismutase activities and carotenoid levels in microalga *Dunaliella saline* CCAP 19/18", Bioresourse Technology, vol. 147, 2013, pp. 23-28.
Sigaud-Kutner, T.C.S., et al., "Changes in superoxide dismutase activity and photosynthetic pigment content during growth of marine phytoplankters in batchcultures", Physiologia Plantarum, vol. 114, No. 4, 2002, pp. 566-571.
Simental-Martínez, J., et al., "Potential application of aqueous two-phase systems and three-phase partitioning for the recovery of superoxide dismutase from a clarified homogenate of Kluyveromyces marxianus", Biotechnology Progress, vol. 30, No. 6, 2014, pp. 1326-1334.
Vieira, L.R., et al., Multiple stress effects on marine planktonic organisms: Influence of temperature on the toxicity of polycyclic aromatic hydrocarbons to Tetraselmis chuii:, Journal of Sea Research, vol. 72, 2012, pp. 94-98.
Boland, M.J. et al. "Extractive purification of enzymes from animal tissue using aqueous two phase systems: pilot scale studies", Journal of Biotechnology 1991, vol. 19, pp. 19-33.
Custódio, L. et al., "Fatty acid composition and biological activities of *Isochrysis galbana* T-ISO, *Tetraselmis* sp. and *Scenedesmus* sp.: possible application in the pharmaceutical and functional food industries", Journal of Applied Phycology, vol. 26, 2014, pp. 151-161.
Debelius, B. et al., "Toxicity and bioaccumulation of copper and lead in five marine microalgae", Ecotoxicology And Environmental Safety, vol. 72, 2009, pp. 1503-1513.
Dickson, D.M.J. et al., "Osmotic Adjustment In Marine Eukaryotic Algae: The Role Inorganic Ions, Quaternary Ammonium, Tertiary Sulphonium And Carbohydrate Solutes II. Prasinophytes And Haptophytes", New Phytologist, vol. 106, No. 4, 1987, pp. 657-666.
Goiris, K. et al, "Antioxidant potential of microalgae in relation to their phenolic and carotenoid content" Journal of Applied Phycology, vol. 24, 2012, pp. 1477-1486.
Marin, N. et al., "Cultivo de Microalgas y el Rotifero *Brachionus plicatilis* a Gran Escala", ACTA Cientifica Venezolana, vol. 45, 1994, pp. 226-230.
Maligan et al., "Identification Of Antioxidant and Antibacteria Activity of Marine Microalgae *Tetraselmis chuii* Extract", In proceeding of: 5th Young Scientist Seminar (Oct. 2011).
Misra, H.P. and Fridovich I., "Purification and Properties of Superoxide Dismutase from a Red Alga, *Porphyridium cruentum*", Journal of Biological Chemistry 1977, vol. 252 (18) 6421-6423.
Okamoto, O.K. and Asano, C.S., et al., "Effects of Cadmium on Growth And Superoxide Dismutase Activity of the Marine Microalga *Tetraselmis gracilis* (Prasinophyceae)", Journal of Phycology, vol. 32, 1996, pp. 74-79.
Perfeto, P.N.M., et al., "Cultivo unialgal de *Tetraselmis chuii* Butcher (Prasinophyceae-Pyramimonadales) com fertilizante Agrícola em diferentes salinidades" Iheringia, No. 48, 1997, pp. 3-14.
Saha, S.K., et al., "Effect of macro- and micro-nutrient limitation on superoxide dismutase activities and carotenoid levels in microalga *Dunaliella salina* CCAP 19/18", Bioresourse Technology, vol. 147, 2013, pp. 23-28.
Sigaud-Kutner, T.C.S., et al., "Changes in superoxide dismutase activity and photosynthetic pigment content during growth of marine phytoplankters in batch-cultures", Physiologia Plantarum, vol. 114, 2002, pp. 566-571.
Ulloa G. et al., On the double role of surfactants as microalga cell lysis agents and antioxidants extractants, Green Chemistry 2012, vol. 14: 1044-1051.
Apr. 4, 2019 Communication pursuant to Article 94(3) EPC which issued in connection with corresponding European Patent Application No. EP16725049.7.
Ghezelbash et al. "Effects of Different Salinities and Luminance on Growth Rate of the Green Microalgae *Tetraselmis chuii*." Research Journal of Biological Sciences, 3 (3): 311-314, 2008.
Chen et al. "The effects of temperature on the growth of and ammonia uptake by marine microalgae", Botanical Studies, 53: 125-133, 2012.
Anonymous: "TetraSOD—80g Marine Phytoplankton 5000 Pure Powder Plankton—Buy Marine Phytoplankton 5000 Supplements",

(56) References Cited

OTHER PUBLICATIONS

Feb. 5, 2015*, Retrieved from the Internet: URL:http://www.marinephytoplankton5000.com/buy-pure-sod-plankton-5000/80-grams-powder-marine-phytoplankton-5000.html [retrieved on Mar. 29, 2019] * earliest date of accession according to http://web.archive.org/web/2015101000000*/http://www.marinephytoplankton5000.com/buy-pure-sod-plankton-5000/80-grams-powder-marine-hytoplankton-5000.html.

K.K.I.U. Arunakumara and Xuecheng Zhang, "Heavy Metal Bioaccumulation and Toxicity with Special Reference to Microalgae", J. Ocean Univ. Chin., vol. 7, No. 1, pp. 25-30 (2008).

Antonio León-Vaz et al., "Effect of cadmium in the microalga *Chlorella sorokiniana*: A proteomic study", Ecotoxicology and Environmetal Safety 207 (2021).

Lin Li et al., "De novo transcriptomic analysis of Chlorella sorokiniana reveals differential genes expression in photosynthetic carbon fixation and lipid production", BMC Microbiology, 16:223, pp. 1-12 (2016).

Jeong-Jin Park et al., "The response of Chlamydomonas reinhardtii to nitrogen deprivation: a systems biology analysis", The Plant Journal (2015).

Ernani Pinto et al., "Heavy Metal-Induced Oxidative Stress In Algae", J. Phycol., 39, pp. 1008-1018 (2003).

Canqi Zheng et al., "Impact of Pb on Chlamydomonas reinhardtii at Physiological and Transcriptional Levels", vol. 11, Article 1443, pp. 1-14 (2020).

\* cited by examiner

Experimental Design

| Runs | PEG % w/w | Pi % w/w | PEG (g) | Pi (g) | Sample | ddH$_2$O | Total weight |
|---|---|---|---|---|---|---|---|
| 1 | 15 | 17 | 0.3 | 0.43 | 0.1 | 0.17 | 1 |
| 2 | 20 | 12 | 0.4 | 0.3 | 0.1 | 0.2 | 1 |
| 3 | 12 | 17 | 0.24 | 0.43 | 0.1 | 0.23 | 1 |
| 4 | 19 | 15 | 0.38 | 0.38 | 0.1 | 0.14 | 1 |
| 5 | 16 | 11 | 0.32 | 0.28 | 0.1 | 0.3 | 1 |
| 6 | 16 | 19 | 0.32 | 0.48 | 0.1 | 0.1 | 1 |
| 7 | 18 | 16 | 0.36 | 0.4 | 0.1 | 0.14 | 1 |
| 8 | 11 | 18 | 0.22 | 0.45 | 0.1 | 0.23 | 1 |
| 9 | 17 | 15 | 0.34 | 0.38 | 0.1 | 0.18 | 1 |
| 10 | 12 | 20 | 0.24 | 0.5 | 0.1 | 0.16 | 1 |
| 11 | 18 | 12 | 0.36 | 0.3 | 0.1 | 0.24 | 1 |
| 12 | 15 | 20 | 0.3 | 0.5 | 0.1 | 0.1 | 1 |
| 13 | 11 | 13 | 0.22 | 0.33 | 0.1 | 0.35 | 1 |
| 14 | 13 | 18 | 0.26 | 0.45 | 0.1 | 0.19 | 1 |
| 15 | 17 | 14 | 0.34 | 0.35 | 0.1 | 0.21 | 1 |
| 16 | 20 | 14 | 0.4 | 0.35 | 0.1 | 0.15 | 1 |
| 17 | 14 | 19 | 0.28 | 0.48 | 0.1 | 0.14 | 1 |
| 18 | 13 | 11 | 0.26 | 0.28 | 0.1 | 0.36 | 1 |
| 19 | 19 | 13 | 0.38 | 0.33 | 0.1 | 0.19 | 1 |
| 20 | 14 | 16 | 0.28 | 0.4 | 0.1 | 0.22 | 1 |

New Experimental Design for further improvement of properties of interest

Selection of best conditions and scale up to final 10 g

Initial small-scale screening in 2 mL tubes at final 1 g weight

Data analysis (U/mg, Purification fold, etc)

METHOD FOR OBTAINING A BIOMASS OF A MICROALGA OF THE SPECIES *TETRASELMIS CHUII* ENRICHED IN SUPEROXIDE DISMUTASE (SOD)

FIELD OF THE INVENTION

The invention relates to a biomass of a microalga of the species *Tetraselmis chuii* enriched in superoxide dismutase (SOD), a method for obtaining same, a method for purifying SOD from said biomass, a protein extract enriched in SOD, and their uses. The invention also relates to the use of a specific brine solution rich in magnesium as a stabiliser of SOD comprised in a biomass of a microalga containing SOD as well as to a biomass of a microalga of the species *T. chuii* enriched in SOD wherein the SOD is stabilised with said brine.

BACKGROUND OF THE INVENTION

Microbial and animal enzymes were once the primary choice of industry, offering economic, functional products of acceptable quality. However, due to negative media attention associated with microbial and animal derived products, consumers are demanding an alternative, Today's food and cosmetic chemists are faced with the challenge to replace traditional animal derived enzymes with others that offer the same functionality but are derived from natural "green" sources (e.g., algae). Microalgae diversity promises to provide new and diverse enzymes and biocatalysts and has the potential to make industrial biotechnology an economic, sustainable success. So far, only a few enzymes have been isolated and characterized from marine phytoplankton. Research has demonstrated the presence of unique haloperoxidases (e.g., vanadium bromoperoxidase with a high degree of stability to thermal and organic solvent denaturation) in algae.

Due to the positive consumer opinion on enzymes, efforts are made to find new areas of application in food and cosmetic products (such as functional foods, nutricosmetics, enzymes in skin protection). Enzymes with the ability to capture free radicals and thereby preventing damage to the skin caused by environmental pollution, bacteria, smoke, sunlight or other harmful factors may be used. In this case, the most protective and promising enzyme is superoxide dismutase (SOD, EC 1.15.1.1).

SOD is an enzyme that catalyzes the dismutation of superoxide into oxygen and hydrogen peroxide and contributes to the important antioxidant defence mechanism in nearly cells exposed to oxygen. SOD is used in cosmetic products to reduce free radical damage to skin. This enzyme is also currently present in clinical trials towards diseases involving oxidative stress and exhibits powerful anti-inflammatory activity. Bovine liver SOD even had regulatory approval in several European countries for such use. However, it was truncated, apparently, by concerns about prion disease. It has been proposed to use a combination of SOD and peroxidase as free radical scavengers in cosmetic products because of their ability to reduce UV-induced erythema when topically applied.

The production and purification of enzymes and extracts containing same from microalgae as well as their applications has been disclosed. By illustrative, ES223450T3 discloses a method for obtaining a thermostable extract from a microalgae culture medium having antioxidant and scar healing activity. The method comprises a first step of culturing said microalgae under appropriate conditions of lighting, temperature, pH and $CO_2$ and a second step of subjecting said culture to oxygen supersaturation. U.S. Pat. No. 5,179,012A teaches a process for producing an extract rich in antioxidants from a microalga culture, wherein the microalgae are cultured in a closed photobioreactor and the oxygen produced by photosynthesis by the microalgae is collected and reinjected it into the culture medium. US2009130139 discloses a cosmetic active ingredient comprising a microalga extract and arginine ferrulate. Okamoto et al. (Okamoto, O K et al., Journal of Phycology 1996, 32: 74-79) teach the effect of the heavy metal cadmium on the growth and SOD production of *Tetraselmis gracilis*. Maligan et al. (Maligan et al., 10/2011; In proceedings of: 5th Young Scientist Seminar) describe the antioxidant and antibacterial activity of an extract of *Tetraselmis chuii*. Misra & Fridovich (Misra, H P and Fridovich I, Journal of Biological Chemistry 1997, 252: 6421-6423) describe a method for purification superoxide dismutase from the red alga *Porphyridium cruentum*. Boland et al. (Boland M J et al., Journal of Biotechnology 1991, 19: 19-33) describe the purification of different enzymes, including SOD, from animal tissues using aqueous two-phase systems. Ulloa et al. (Ulloa G et al., Green Chemistry 2012, 14: 1044-1051) describe a surfactant/salt two-phase aqueous partition system for the extraction of antioxidants from the microalga *Tetraselmis suecica*.

Although the production and purification of enzymes and extracts containing same from microalgae is known, the SOD activity recovered in prior art methods is, generally, low. Thus there exists the need of providing methods that allow for the production and purification of enzymes, particularly SOD activity, in greater amounts and with higher yield.

SUMMARY OF THE INVENTION

The production of SOD in different species of microalgae under different culture systems and conditions has been studied. To that end, a total of 11 microalga strains were tested under different abiotic stress conditions in different culturing system including indoor and outdoor cultures to see how these affect the SOD activity of the different strains. *Tetraselmis chuii* was found to have the highest SOD activity in all the abiotic conditions tested, although the highest activity was obtained under nitrogen starvation (Example 1).

Further, different PEG-phosphate aqueous two-phase systems were developed, as an economic extraction strategy for the fractionation and partial purification of SOD activity from the *T. chuii* cell free extract. A detailed study was carried out to analyze the effect of PEG molar mass, concentration, pH and ionic composition in the system on the partitioning behavior of superoxide dismutase activity in the phosphate rich phase. Two polyethyleneglycol/phosphate (PEG/Pi) aqueous two-phase systems composed of: PEG 1500: 12% w/w PEG, 20% w/w Pi supplemented with 10% w/w NaCl, and PEG 3000: 12% w/w PEG, 20% w/w Pi supplemented with 3.5% w/w NaCl were selected as the systems with the highest selectivity of SOD over native microalgae total proteins (Example 2). Under these conditions, sufficient purification (2-4 fold) with high recovery (>80%) was achieved for SOD at the bottom phosphate phase. In addition, the system allows removal of unwanted low molecular weight compounds, such as chlorophylls and polyphenols. The SOD/phosphate phase exhibits high thermostability at 50° C. and 60° C.

Further, in vitro toxicity assays, demonstrated that the *T. chuii* cell free extract could effectively protect human primary skin fibroblast against oxidative damage caused by $H_2O_2$ (Example 3).

Therefore, in a first aspect, the invention relates to a method for obtaining a biomass of a microalga of the species *T. chuii* enriched in SOD which comprises culturing said microalga under abiotic stress, wherein said abiotic stress is selected from the group consisting of a redox potential of at least 100 mV in the culture medium, a temperature greater than 28° C. in the culture medium, nitrogen starvation and a salinity greater than 35 in the culture medium.

In a second aspect, the invention relates to a method for enriching superoxide dismutase (SOD) in a biomass of a microalga of the species *Tetraselmis chuii* which comprises culturing said microalga under abiotic stress.

In another aspect, the invention relates to a biomass of a microalga of the species *T. chuii* enriched in SOD obtained by the method of the first aspect or a biomass of a microalga of the species *T. chuii* enriched in SOD by the method of the second aspect.

In another aspect, the invention relates to a dehydrated or brine-treated biomass of a microalga of the species *T. chuii* enriched in SOD.

In another aspect, the invention relates to a method for purifying SOD from said biomass of a microalga of the species *T. chuii*, comprising the steps of
  (i) homogenising said biomass of a microalga of the species *T. chuii* thereby obtaining a homogenate, and
  (ii) fractionating the homogenate obtained in step (i) by polyethyleneglycol (PEG)/phosphate aqueous two-phase partition system, thereby obtaining a protein extract enriched in SOD in the phosphate aqueous fraction.

In another aspect, the invention relates to a protein extract enriched in SOD obtained by said SOD purification method.

In another aspect, the invention relates to a foodstuff comprising said biomass of a microalga of the species *T. chuii* enriched in SOD, or said dehydrated or brine-treated biomass of a microalga of the species *T. chuii* enriched in SOD, or said protein extract enriched in SOD.

In another aspect, the invention relates to a pharmaceutical composition comprising said biomass of a microalga of the species *T. chuii* enriched in SOD, or said dehydrated or brine-treated biomass of a microalga of the species *T. chuii* enriched in SOD, or said protein extract enriched in SOD.

In another aspect, the invention relates to the use of said biomass of a microalga of the species *T. chuii* enriched in SOD, or of said dehydrated or brine-treated biomass of a microalga of the species *T. chuii* enriched in SOD, or of said protein extract enriched in SOD, or of said pharmaceutical composition as a cosmetic.

In another aspect, the invention relates to the use of said biomass of a microalga of the species *T. chuii* enriched in SOD, or of said dehydrated or brine-treated biomass of a microalga of the species *T. chuii* enriched in SOD, or of said protein extract enriched in SOD, or of said pharmaceutical composition as an antioxidant.

In another aspect, the invention relates to said biomass of a microalga of the species *T. chuii* enriched in SOD, or of said dehydrated or brine-treated biomass of a microalga of the species *T. chuii* enriched in SOD, or of said protein extract enriched in SOD, or of said pharmaceutical composition for use in medicine.

In another aspect, the invention relates to said biomass of a microalga of the species *T. chuii* enriched in SOD, or of said dehydrated or brine-treated biomass of a microalga of the species *T. chuii* enriched in SOD, or of said protein extract enriched in SOD, or of said pharmaceutical composition for use in the prevention and/or treatment of a disease or condition characterised by an oxidative stress and/or an inflammatory activity, or in improving tolerance to radiation therapy.

In another aspect, the invention relates to the use of a brine comprising between 10 and 18 g/L total sulphur (S), between 40 and 55 g/L sulphate ($SO_4^{2-}$), between 60 and 1,500 mg/L calcium ($Ca^{2+}$), between 52 and 70 g/L magnesium ($Mg^{2+}$), between 15 and 20 g/L potassium ($K^+$), between 9 and 20 g/L potassium ($Na^+$), between 115 and 180 g/L chloride ($Cl^-$) and having a density between 1.25 and 1.30 g/ml at 20° C. as a stabiliser of SOD comprised in a biomass of a microalga containing SOD. In a particular embodiment, said biomass of a microalga containing SOD is the biomass of a microalga of the species *T. chuii* enriched in SOD.

In another aspect, the invention relates to a biomass of a microalga of the species *T. chuii* enriched in SOD characterised in that the SOD is stabilised with a brine, wherein the brine comprises between 10 and 18 g/L total sulphur (S), and between 40 and 55 g/L sulphate ($SO_4^{2-}$), and between 60 and 1,500 mg/L calcium ($Ca^{2+}$), and between 52 and 70 g/L magnesium ($Mg^{2+}$), and between 15 and 20 g/L potassium ($K^+$), and between 9 and 20 g/L potassium ($Na^+$), and between 115 and 180 g/L chloride ($Cl^-$) and having a density between 1.25 and 1.30 g/ml at 20° C.

DETAILED DESCRIPTION OF THE INVENTION

Figure 1:
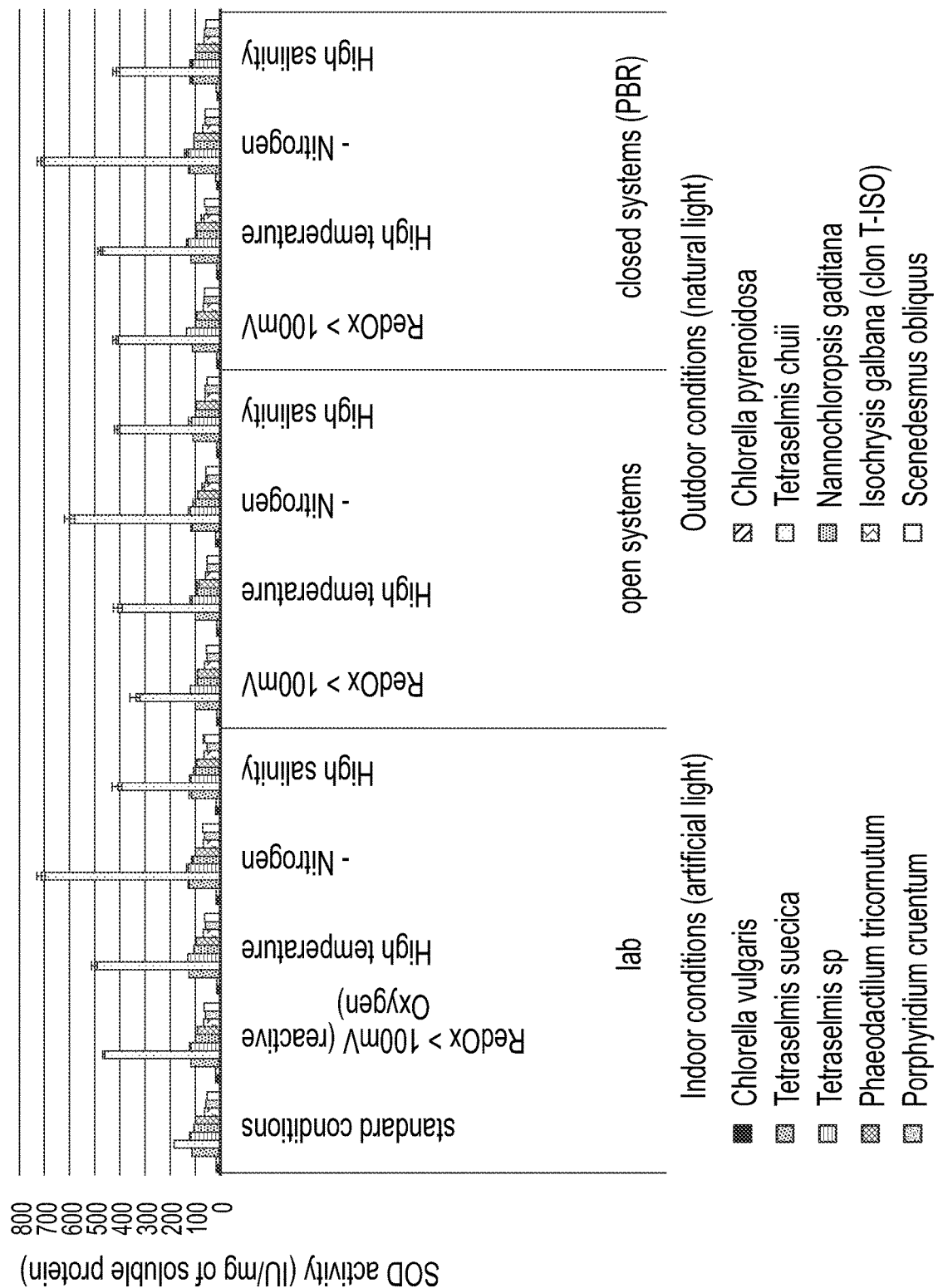
FIG. 1 is a bar diagram showing the SOD activity for the different strains tested under the different treatments as described in Table 1 (Example 1).

Method for Obtaining a Biomass of a Microalga of the Species *Tetraselmis chuii* Enriched in SOD In an aspect, the invention relates to a method for obtaining a biomass of a microalga of the species *Tetraselmis chuii* enriched in SOD, hereinafter referred to as the "production method of the invention", which comprises culturing said microalga under abiotic stress, wherein said abiotic stress is selected from the group consisting of a redox potential of at least 100 mV in the culture medium, a temperature greater than 28° C. in the culture medium, nitrogen starvation and a salinity greater than 35 in the culture medium.

*Tetraselmis chuii*, o *T. chuii*, is a marine unicellular alga (microalga) belonging to the Chlorodendrophyceae class, Chlorodendrales order, Chlorodendraceae family; it is green, motile and usually grows 10 μm long×14 μm wide.

According to the production method of the invention, the microalga *T. chuii* is cultured under abiotic stress. Before applying the abiotic stress, culture of *T. chuii* is performed in a suitable medium, such as, for example, in F/2 culture medium [Guilard R. R. L. & Ryther, J. H. 1962. "Studies of marine planktonic diatoms. I. Cyclotela nana Hustedt and Detonula confervaceae (Cleve) Gran." Can. J. Microbiol. 8, 229-239], under solar or proper lighting conditions (luminous intensity) and controlled conditions of pH, temperature and feed carbon dioxide ($CO_2$), as it is well-known for the skilled person in the art. The F/2 culture medium comprises a source of nitrogen, a source of phosphorus, trace elements such as, for example, sodium, iron, copper, zinc, cobalt, manganese and molybdenum as well as a mix of vitamins such, for example, cyanocobalamin (vitamin B12), thiamine (vitamin B1) and biotin in an aqueous medium.

Luminous intensity is regulated so that photosynthesis is allowed; thus, although it can vary within a broad range, in a particular embodiment, luminous intensity applied to the culture medium is comprised between 60 and 2000 μmol fotons $m^{-2}$ $s^{-1}$, indoor typically about 150 μmol fotons $m^{-2}$ $s^{-1}$. pH can vary usually between about 7 and about 8.5, typically about 7.5. A temperature promoting the growth of *T. chuii* is selected usually comprised between about 17° C. and about 28° C., typically between about 24° C. and 26° C. Culture is performed with or without aeration, typically with aeration, for example, with approximately 0.5 to 5, preferably about 1-2% $CO_2$ in atmospheric air.

When the cell density of the culture medium is optimal, what normally occurs during the log, or exponential growth, phase, i.e., about 2 to 7 days after starting cultivation, the abiotic stress is applied to the culture medium. To that end, growth rates can be monitored by conventional techniques, for example, by microscopy cell counts.

As used herein, the expression "abiotic stress" relates to the negative impact of non-living factors on the living organisms in a specific environment. The non-living variable must influence the environment beyond its normal range of variation to adversely affect the population performance or individual physiology of the organism in a significant way.

There are a lot of abiotic stress factors that can affect the growth of microalgae, e.g., *T. chuii*, and the production of compounds and metabolites thereof; nevertheless, in the production method of the invention, the abiotic stress is selected from the group consisting of a redox potential of at least 100 mV in the culture medium, a temperature greater than 28° C. in the culture medium, nitrogen starvation and a salinity greater than 35 in the culture medium.

According to the invention, an abiotic stress based a redox potential of at least 100 mV in the culture medium comprises maintaining the culture medium with a redox potential of at least 100 mV, at least 200 mV, at least 300 mV, at least 400 mV, at least 500 mV, at least 600 mV, at least 700 mV, at least 800 mV at least 900 mV, at least 1000 mV; said abiotic stress can be obtained by conventional methods for obtaining high redox potential conditions in culture media, such as, for example, by the addition of ozone which is normally generated using an ozone generator by reaction of the air with UV. The amount of ozone to be added is the necessary to achieve and maintain the culture medium with a redox potential of at least 100 mV, at least 200 mV, at least 300 mV, at least 400 mV, at least 500 mV, at least 600 mV, at least 700 mV, at least 800 mV at least 900 mV, at least 1000 mV.

An abiotic stress based on a temperature greater than 28° C., according to the invention, comprises maintaining the culture medium at a temperature of at least 28° C., at least 30° C., at least 35° C., at least 40° C., at least 45° C., at least 50° C.; said temperature in the culture medium can be obtained by conventional methods. Since the culture can be indoor or outdoor, for indoor cultures, the temperature of the culturing room must be set above 28° C.; whereas for outdoor cultures, the culture should be done in appropriate locations wherein said temperature is reached naturally by the environmental temperature, for example during Spring and Summer in Southern Spain, e.g., Cádiz, Málaga, Sevilla, etc.

According to the invention, an abiotic stress based on a salinity greater than 35 in the culture medium comprises maintaining the culture medium with a salinity of at least 35 PSU (practical salinity units), at least 40 PSU, at least 41

PSU, at least 45 PSU, at least 50 PSU, at least 100, at least 200, at least 300. In a particular embodiment, the salinity in the culture medium is greater than 41 PSU. The skilled person knows how to determine the salinity of the culture medium by using standard techniques (UNESCO, 1981, "Background papers and supporting data on the practical salinity scale 1978" Unesco Technical papers in marine science, 37). An abiotic stress based on high salinity condition can be obtained easily by adding salts to said culture medium until said salinity condition is reached, for example, by evaporating natural seawater until de target salinity is reached or by adding commercially available sea salts.

An abiotic stress based on nitrogen starvation, according to the invention, comprises growing *T. chuii* under conditions of nitrogen deficiency, limitation or privation; said abiotic stress can be achieved easily by stopping the supply of nitrogen to the culture medium (i.e., by refraining from adding nitrogen to the culture medium).

In a preferred embodiment of the production method of the invention, the abiotic stress comprises nitrogen starvation. The twin "nitrogen starvation", as used herein, refers to a condition in which the supply of nitrogen is such that the nitrate concentration in the culture medium is less than 200 µM, less than 100 µM, less than 10 µM, less than 5 µM, less than 1 µM, less than 0.1 µM, less than 0.001 µM or a condition in which the supply of nitrogen is such that the nitrogen concentration in the culture medium is less than 10 µg/ml, less than 5 µg/ml, less than 3 µg/ml, less than 1 µg/ml, less than 0.1 µg/ml, less than 0.08 µg/ml, less than 0.05 µg/ml, less than 0.001 µg/ml. In a particular embodiment, the nitrogen starvation means a nitrate concentration in the culture medium of less than 5 µM. In another particular embodiment, the nitrogen starvation means a nitrogen concentration in the culture medium of less than 10 µg/ml. In another particular embodiment, when the only source of nitrogen is nitrate, nitrogen starvation means a nitrate concentration in the culture medium of less than less than 200 µM, less than 100 µM, less than 10 µM, less than 5 µM, less than 1 µM, less than 0.1 µM or less than 0.001 µM, preferably less than 5 µM.

Cultivation of *T. chuii* can be operated in continuous, semi-continuous, batch or fed-batch mode. In a particular embodiment, cultivation of *T. chuii* is operated in fed-batch mode in order to prevent nutrient limitation.

Cultures of *T. chuii* can be performed indoor or outdoor. Outdoor cultures can be performed in either open or closed systems.

Open systems include raceway ponds which are about 20 to 35 cm deep to ensure adequate exposure to sunlight. Paddlewheels provide motive force and keep the microalgae suspended in the water. The ponds are supplied with water and nutrients.

Closed systems include tubular photobioreactors (PBR) which usually consist of a pump that drives the culture medium through a horizontal tubular solar receiver. A PBR provides a controlled environment and enables high productivity of microalgae. As it is a closed system, all growth requirements of microalgae are introduced into the system and controlled according to the requirements. PBRs facilitate better control of culture environment such as carbon dioxide supply, water supply, optimal temperature, efficient exposure to light, culture density, pH levels, gas supply rate, mixing regime, etc.

According to the production method of the invention, once *T. chuii* has been cultured under abiotic stress, a biomass of microalga *T. chuii* enriched in SOD is produced.

The term "biomass", as used herein, includes biological material comprising, living or recently living organisms. By extension, the term includes not only the biological material or organic matter which constitutes an organism, but also the biological material or organic matter generated in a biological process, spontaneous or not spontaneous (i.e., provoked).

The expression "biomass of a microalga of the species *T. chuii* enriched in SOD" refers to a biomass of *T. chuii* having a SOD activity higher than that corresponding to a biomass of *T. chuii* of reference. Since *T. chuii* produces SOD when cultured under standard conditions, a "biomass of *T. chuii* of reference" is a biomass obtained by culturing *T. chuii* under standard conditions, i.e., by culturing *T. chuii* in F/2 culture medium at 150 µmol fotons $m^{-2}$ $s^{-1}$, at a temperature between 24° C. and 26° C., at pH 7.5, and with 1-2% $CO_2$ enriched atmospheric air. Under these conditions, a culture of *T. chuii* provides a biomass showing a SOD activity of about 180 IU/mg of soluble protein when determined by following the inhibition of the rate of reduction of cytochrome c in a coupled system, using xanthine and xanthine oxidase at 216 mM Pi, pH 7.8, 25° C., as described in Example 1. Thus, a biomass of a microalga of the species *T. chuii* enriched in SOD normally shows a SOD activity equal to or higher than 180 IU/mg of soluble protein, usually equal to or higher than 200 IU/mg of soluble protein, typically equal to or higher than 250 IU/mg of soluble protein, when SOD activity is assayed following the above mentioned method. In one embodiment, the biomass of a microalga of the species *T. chuii* is enriched in SOD when the SOD activity is at least 10%, at least 20%, at least 30%, at least 40%, at least 50%, at least 60%, at least 70%, at least 80%, at least 90%, at least 100%, at least 200%, at least 300%, at least 400%, at least 500%, at least 600%, at least 700%, at least 800%, at least 900%, at least 1000% or more with respect to the SOD activity in a biomass of reference as defined above.

Once *T. chuii* has been cultured under abiotic stress conditions according to the production method of the invention, the resulting biomass of *T. chuii* enriched in SOD is collected from the culture and stabilized. Biomass of *T. chuii* enriched in SOD so produced can be collected by conventional methods known for the skilled person in the art, such as, for example, by filtration or centrifugation; then, the collected biomass is preferably and advantageously washed to remove non-biological material (e.g., mineral salt precipitates and the like). Subsequently, the biomass is stabilized either by dehydration or by adding said biomass to a brine solution rich in magnesium. The term "dehydration" refers to a partial and/or complete removal of the water of the biomass. For example, the amount of water removed from the biomass may be of at least 10%, at least 20%, at least 30%, at least 40%, at least 50%, at least 60%, at least 70%, at least 80%, at least 90%, at least 99% or 100% of the water originally contained in the biomass. The dehydration of the biomass can be performed by any suitable method, for example, by freeze-drying or by spray-drying.

In a particular embodiment, the dehydration is performed by freeze-drying. The term "freeze-drying" or "lyophilisation" as used herein, refers the removal of water by the technique of sublimation and removal of water vapor under vacuum, i.e., the direct passage of the frozen water from the solid state to the vapor state and the subsequent removal of the vapor.

In another particular embodiment, the dehydration is performed by spray drying. The term "spray-drying" refers to a dehydrating method comprising breaking up liquid mixtures into small droplets (atomization) and rapidly removing solvent from the mixture in a container (spray-drying apparatus) where there is a strong driving force for evaporation of solvent from the droplets. The spray-drying of the biomass can be performed, for example, using a BUCHI Mini Spray dryer B-290, injecting with the pump at 40% rate a 10% dry weight product solution, the inlet temperature setting at 130° C., the outlet temperature dropping below 60° C. and the aspirator setting at 100% rate.

In a particular embodiment, the biomass is stabilized by adding said biomass to a brine solution rich in magnesium. Said brine solution rich in magnesium comprises between 10 and 18 g/L total sulphur (S), between 40 and 55 g/L sulphate ($SO_4^{2-}$), between 60 and 1,500 mg/L calcium ($Ca^{2+}$), between 52 and 70 g/L magnesium ($Mg^{2+}$), between 15 and 20 g/L potassium ($K^+$), between 9 and 20 g/L potassium ($Na^+$); between 115 and 180 g/L chloride ($Cl^-$), and has a density between 1.25 and 1.30 g/ml at 20° C. Said brine solution rich in magnesium, whose particulars will be discussed below, can be used therefore as a stabiliser of SOD comprised in a biomass of a microalga containing SOD.

Once the microalgal biomass has been stabilized, the SOD activity of the biomass can be determined. Although different methods and kits for the determination of SOD activity can be followed, in a particular embodiment, SOD activity of the biomass is determined by following the inhibition of the rate of reduction of cytochrome c in a coupled system, using xanthine and xanthine oxidase at 216 mM Pi, pH 7.8, 25° C., as described in Example 1.

According to the production method of the invention, a biomass of *T. chuii* enriched in SOD is obtained showing a SOD activity greater than 180 IU/mg of soluble protein when determined by following the inhibition of the rate of reduction of cytochrome c in a coupled system, using xanthine and xanthine oxidase at 216 mM Pi, pH 7.8, 25° C., as described in Example 1, depending on the abiotic stress used; thus, as it is shown in FIG. 1, on average:

- when *T. chuii* is cultured under conditions of nitrogen starvation, a biomass of *T. chuii* enriched in SOD is obtained showing a SOD activity comprised between about 700 and about 730 IU/mg of soluble protein;
- when *T. chuii* is cultured under conditions of high temperature, a biomass of *T. chuii* enriched in SOD is obtained showing a SOD activity comprised between about 487.50 and 512.5 IU/mg of soluble protein;
- when *T. chuii* is cultured under conditions of high salinity, a biomass of *T. chuii* enriched in SOD is obtained showing a SOD activity comprised between about 391.10 and 428.9 IU/mg of soluble protein; and
- when *T. chuii* is cultured under conditions of high redox potential, a biomass of *T. chuii* enriched in SOD is obtained showing a SOD activity comprised between about 454.7 and 465.3 IU/mg of soluble protein.

Method for Enriching a Biomass of *T. chuii* in SOD

In another aspect, the invention relates to a method for enriching a biomass of a microalga of the species *Tetraselmis chuii* in superoxide dismutase (SOD), hereinafter "enriching method of the invention", which comprises culturing said microalga under abiotic stress.

The terms "biomass of a microalga of the species *T. chuii*" and "SOD" as well as the culture conditions for *T. chuii* before applying the abiotic stress have been previously defined in connection with the production method of the invention.

The term "abiotic stress" relates to the negative impact of non-living factors on the living organisms in a specific environment. The non-living variable must influence the environment beyond its normal range of variation to adversely affect the population performance or individual physiology of the organism in a significant way. In a particular embodiment, the abiotic stress is selected from the group consisting of high redox potential, high temperature, high salinity and nitrogen starvation.

According to the invention, an abiotic stress based on a high redox potential comprises maintaining the culture medium with a redox potential of at least 100 mV, at least 200 mV, at least 300 mV, at least 400 mV, at least 500 mV, at least 600 mV, at least 700 mV, at least 800 mV at least 900 mV, at least 1000 mV. Methods for obtaining said abiotic stress have been previously defined.

An abiotic stress based on high temperature comprises maintaining the culture medium at a temperature of at least 28° C., at least 30° C., at least 35° C., at least 40° C., at least 45° C., at least 50° C. Methods for obtaining said high temperature have been previously defined.

According to the invention, an abiotic stress based on a high salinity condition comprises maintaining the culture medium with a salinity of at least 35 PSU (practical salinity units), at least 41 PSU, at least 40 PSU, at least 45 PSU, at least 50 PSU, at least 100, at least 200, at least 300. In a particular embodiment, the salinity in the culture medium is greater than 41 PSU. Methods for obtaining said high salinity have been previously defined.

An abiotic stress based on nitrogen starvation has been previously defined in connection with the production method of the invention.

Biomass of *T. chuii* Enriched in SOD

In another aspect, the invention relates to a biomass of a microalga of the species *T. chuii* enriched in SOD, hereinafter referred to as the "biomass of *T. chuii* enriched in SOD of the invention", obtained by the production method of the invention or enriched in SOD by the enriching method of the invention.

As mentioned above, the biomass of *T. chuii* enriched in SOD of the invention shows a SOD activity greater than 180 IU/mg of soluble protein, normally equal to or higher than 200, typically equal to or higher than 250, usually equal to or higher than 300, preferably equal to or higher than 350, more preferably equal to or higher than 400, still more preferably equal to or higher than 450, even still more preferably equal to or higher than 500, such as equal to or higher than 550, equal to or higher than 600, equal to or higher than 650, equal to or higher than 700 IU/mg of soluble protein, when determined by following the inhibition of the rate of reduction of cytochrome c in a coupled system, using xanthine and xanthine oxidase at 216 mM Pi, pH 7.8, 25° C., as described in Example 1.

In a particular embodiment, the biomass of *T. chuii* enriched in SOD obtained by the production method of the invention is obtained by culturing *T. chuii* under conditions of nitrogen starvation, preferably at a nitrate concentration in the culture medium of less than 5 μM In a more particular embodiment, the biomass of *T. chuii* enriched in SOD of the invention is obtained by culturing *T. chuii* under conditions of nitrogen starvation, preferably at a nitrate concentration in the culture medium of less than 5 μM, and shows a SOD activity comprised between about 700 and about 730 IU/mg of soluble protein.

In another particular embodiment, the biomass of *T. chuii* enriched in SOD obtained by the production method of the invention is obtained by culturing *T. chuii* under conditions of temperature greater than 28° C. In a more particular embodiment, the biomass of *T. chuii* enriched in SOD of the invention is obtained by culturing *T. chuii* under conditions of temperature greater than 28° C. and shows a SOD activity comprised between about 487.50 and 500.5 IU/mg of soluble protein.

In another particular embodiment, the biomass of *T. chuii* enriched in SOD obtained by the production method of the invention is obtained by culturing *T. chuii* under conditions of salinity greater than 35 in the culture medium. In a more particular embodiment, the biomass of *T. chuii* enriched in SOD of the invention is obtained by culturing *T. chuii* under conditions of salinity greater than 35 in the culture medium and shows a SOD activity comprised between about 391.10 and 428.9 IU/mg of soluble protein.

In another particular embodiment, the biomass of *T. chuii* enriched in SOD obtained by the production method of the invention is obtained by culturing *T. chuii* under conditions of redox potential of at least 100 mV. In a more particular embodiment, the biomass of *T. chuii* enriched in SOD of the invention is obtained by culturing *T. chuii* under conditions of redox potential of at least 100 mV and shows a SOD activity comprised between about 417 and 460 IU/mg of soluble protein.

In a particular embodiment, the biomass of *T. chuii* enriched in SOD by the enriching method of the invention is obtained by culturing *T. chuii* under conditions of nitrogen starvation, preferably at a nitrate concentration in the culture medium of less than 5 µM In a more particular embodiment, the biomass of *T. chuii* enriched in SOD of the invention is obtained by culturing *T. chuii* under conditions of nitrogen starvation, preferably at a nitrate concentration in the culture medium of less than 5 µM, and shows a SOD activity comprised between about 700 and about 730 IU/mg of soluble protein.

In another particular embodiment, the biomass of *T. chuii* enriched in SOD by the enriching method of the invention is obtained by culturing *T. chuii* under conditions of high temperature. In a more particular embodiment, the biomass of *T. chuii* enriched in SOD of the invention is obtained by culturing *T. chuii* under conditions of high temperature and shows a SOD activity comprised between about 487.50 and 500.5 IU/mg of soluble protein.

In another particular embodiment, the biomass of *T. chuii* enriched in SOD by the enriching method of the invention is obtained by culturing *T. chuii* under conditions of high salinity. In a more particular embodiment, the biomass of *T. chuii* enriched in SOD of the invention is obtained by culturing *T. chuii* under conditions high salinity and shows a SOD activity comprised between about 391.10 and 428.9 IU/mg of soluble protein.

In another particular embodiment, the biomass of *T. chuii* enriched in SOD by the enriching method of the invention is obtained by culturing *T. chuii* under conditions of high redox potential. In a more particular embodiment, the biomass of *T. chuii* enriched in SOD of the invention is obtained by culturing *T. chuii* under conditions of high redox potential and shows a SOD activity comprised between about 417 and 460 IU/mg of soluble protein.

The biomass of *T. chuii* enriched in SOD of the invention exerts a protective effect against oxidative damage elicited by $H_2O_2$. Thus, it can be used as an antioxidant, as an anti-inflammatory agent, and the like, in the cosmetic or pharmaceutical industries as a cosmetic active ingredient or as a pharmaceutical active ingredient; in addition, the biomass of *T. chuii* enriched in SOD of the invention can be used in the manufacture of foodstuffs comprising said biomass.

Stabilized Biomass of *T. chuii* Enriched in SOD of the Invention

As mentioned above, the biomass of a microalga of the species *T. chuii* enriched in SOD, i.e., the biomass of *T. chuii* enriched in SOD of the invention, can be stabilized either by freeze-drying or by adding said biomass to a brine solution rich in magnesium.

Therefore, in another aspect, the invention relates to a dehydrated or brine-treated biomass of a microalga of the species *T. chuii* enriched in SOD, hereinafter referred to as the "stabilized biomass of *T. chuii* enriched in SOD of the invention".

The particulars of the biomass of *T. chuii* enriched in SOD of the invention have been previously mentioned and are incorporated herein by reference.

In a particular embodiment, the biomass of *T. chuii* enriched in SOD of the invention is stabilized by freeze-drying. The freeze-drying process can be carried out in either manifold or tray type freeze-dryers. These have a vacuum pump to reduce pressure to values below the ambient pressure and a condenser cooled to temperatures between −35 to −80° C. The biomass is frozen and the freeze-drying process starts at −35° C. The temperature is increased slowly, up to 20-30° C., during several days until all the water is removed from the biomass.

In another particular embodiment, the biomass of *T. chuii* enriched in SOD of the invention is stabilized by adding said biomass to a brine solution rich in magnesium. In a particular embodiment, said brine solution rich in magnesium comprises between 10 and 18 g/L total sulphur (S), between 40 and 55 g/L sulphate ($SO_4^{2-}$), between 60 and 1,500 mg/L calcium ($Ca^{2+}$), between 52 and 70 g/L magnesium ($Mg^{2+}$), between 15 and 20 g/L potassium ($K^+$), between 9 and 20 g/L potassium ($Na^+$); between 115 and 180 g/L chloride ($Cl^-$), and has a density between 1.25 and 1.30 g/ml at 20° C.

The stabilized biomass of *T. chuii* enriched in SOD of the invention can be used in the same uses and applications as those previously mentioned in connection with the biomass of *T. chuii* enriched in SOD of the invention.

Method for the Purification of SOD

An extraction strategy for the fractionation and partial purification of SOD activity from *T. chuii* biomass has been developed by inventors, namely a system based on polyethyleneglycol/phosphate (PEG/Pi) aqueous two-phase system (ATPS). The ATPS system has the advantage that the phosphate fraction containing the SOD activity is practically devoid of any of low molecular weight compounds, such as pigments (chlorophyll) and polyphenols, which are unwanted in the SOD preparation.

Thus, in another aspect, the invention relates to a method for purifying SOD from a biomass of a microalga of the species *T. chuii* enriched in SOD obtained by the production method of the invention, or enriched in SOD by the enriching method of the invention, hereinafter referred to as the "SOD purification method of the invention", comprising the steps of:
  (i) homogenising said biomass of a microalga of the species *T. chuii* thereby obtaining a homogenate, and (ii) fractionating the homogenate obtained in step (i) by polyethyleneglycol/phosphate aqueous two-phase partition system, thereby obtaining a protein extract enriched in SOD in the phosphate aqueous fraction.

As used within the context of the SOD purification method of the invention, said biomass of a microalga of the species *T. chuii* is selected from the group consisting of the biomass of a microalga of the species *T. chuii* enriched in SOD (i.e., the biomass of *T. chuii* enriched in SOD of the invention) and the dehydrated or brine-treated biomass of a microalga of the species *T. chuii* enriched in SOD (i.e., the stabilized biomass of *T. chuii* enriched in SOD of the invention).

The particulars of the biomass of *T. chuii* enriched in SOD of the invention as well as the particulars of the stabilized biomass of *T. chuii* enriched in SOD of the invention have been previously mentioned and are incorporated herein by reference.

According to step (i) of the SOD purification method of the invention, a biomass of a microalga of the species *T. chuii* is homogenised thereby obtaining a homogenate. Homogenisation of a biomass of a microalga of the species *T. chuii* can be performed by conventional methods, for example, sonication, high-pressure homogenization, bead-milling or, in general, any method that mechanically lyses the cells. In a particular embodiment, homogenisation of the biomass of a microalga of the species *T. chuii* is performed by adding an extraction buffer to said biomass and lysing the microalga cells. Although different extraction buffers can be potentially used, in a particular embodiment, said extraction buffer has a pH of 7.8 and comprises 220 mM $KH_2PO_4$. The microalga cells can be lysed by conventional methods, for example, by ultrasounds; in a particular embodiment, cells are lysed by applying ultrasounds for 2 min with 10 seconds intervals (4 cycles of 30 sec each, 20% amplification). The biomass is then removed and the supernatant collected. Removal of the biomass can be performed by conventional methods, for example, by centrifugation; in a particular embodiment, the biomass is centrifuged at 16,000 rpm for 10 min at room temperature and the supernatant is collected.

According to step (ii) of the SDO purification method of the invention, the homogenate obtained in step (i) is fractionated by means of a polyethyleneglycol/phosphate (PEG/Pi) aqueous two-phase partition system, sometimes referred to as "PEG/Pi ATPS", thereby obtaining a protein extract enriched in SOD in the phosphate aqueous fraction.

A PEG/Pi ATPS can be prepared from a 50% (w/w) PEG stock solution and from a 40% (w/w) of a potassium phosphate stock solution, pH 7.0.

The PEG stock solution can be prepared by dissolving the calculated amount of PEG in deionized water. In the present description, the term "polyethyleneglycol" or "PEG" is understood to be any hydrophilic polymer soluble in water containing ether groups linked by 2 carbon atoms, optionally branched alkylene groups. The structure of PEG is (note the repeated element in parentheses):

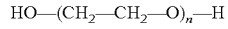

HO—(CH$_2$—CH$_2$—O)$_n$—H wherein "n" is the number of EO monomers or units.

Therefore this definition includes branched or non-branched polyethyleneglycols, and also block or random copolymers including said type of units. The term also includes derivatives of the terminal hydroxyl groups, which can be modified (one or both ends) so as to introduce alkoxy, acrylate, methacrylate, alkyl, amino, phosphate, isothiocyanate, sulfhydryl, mercapto and sulfate groups. The polyethyleneglycol can have substituents in the alkylene groups. If they are present, these substituents are preferably alkyl groups.

The average molecular weight of PEG for use in the SOD purification method of the invention can vary within a broad range; nevertheless, in a particular embodiment, the PEG has an average molecular weight comprised between 1500 and 6000 Da, preferably between 1500 and 3000 Da. In a preferred embodiment, the PEG has an average molecular weight of 3000 Da.

The potassium phosphate solution can be prepared at a proportion of 7:18 monobasic: dibasic by dissolving the calculated amounts of anhydrous monobasic potassium phosphate and anhydrous dibasic potassium phosphate in deionized water, and adjusting pH to 7.0 if necessary by using a base, for example, NaOH or an acid, for example, HCl.

Since the distribution of a particular protein in a two-phase partition system depends on its unique physicochemical properties, such as size, surface charge, hydrophobicity, etc., if properly optimized, e.g., by careful adjustment of the factors that influence the distribution of proteins, such as particulars of the components of the two-phase partition system, ionic strength, pH, etc., many of the shortcomings of centrifugation and ultrafiltration, commonly used at the initial stages of extraction can be circumvented thus rendering a partially purified and concentrated final product.

In one embodiment, once the homogenate obtained in step (i) has been extracted using the ATPS, the phase containing the protein extract enriched in SOD in the phosphate aqueous fraction has to be separated from the phase containing the PEG. In one embodiment, the phases are separated using centrifugation. In another embodiment, the two phases (PEG and Pi), as well as the interface between them, are allowed to form without centrifugation. This would facilitate large scale purification and lower the cost of the process.

Therefore, considering that the PEG/Pi ATPS parameters, such as PEG average molecular weight of PEG, concentration, salt composition and pH in the PEG/Pi ATPS, have a great impact on the protein distribution (Kp, partition coefficient), i.e., partitioning behavior of SOD activity in the Pi phase, and the total yield, a factorial experiment was designed and several different conditions were screened (Example 2). Those conditions which resulted in the formation of distinct and separated PEG and Pi phases were analyzed for SOD activity in the Pi phase after addition to the *T. chuii* homogenate obtained in step (i) to generate the biphasic system (PEG/Pi ATPS). The best conditions with respect to the fold-purification of SOD in the Pi phase were selected for further improvements.

Thus, initially, different PEG/Pi ATPS containing PEG of different average molecular weights and different ratios PEG/Pi phases were tested. To that end, PEG having different average molecular weights (1500, 3000 and 6000 Da) and ranges of PEG and Pi—between 11% and 20% (w/w) in the presence of the *T. chuii* homogenate obtained in step (i) to generate the different biphasic systems (PEG/Pi ATPS) were tested and the Pi phases were analyzed for SOD activity. Subsequently, the best conditions with respect to the fold-purification of SOD activity in the Pi phase were selected and further tests were performed by generating additional PEG/Pi ATPS using different pH values (6.5, 7, 7.5, 8 and 8.5) and different concentrations of NaCl (0% w/w, 3.5% w/w, 7% w/w and 10% w/w). After addition of the *T. chuii* homogenate obtained in step (i) the SOD activity was determined in the Pi phase. In all cases, the different PEG/Pi ATPS were prepared by mixing the components, preferably gently at a temperature comprised between 22° C. and 25° C.; if necessary, a low-speed centrifugation can be performed in order to achieve a complete phase separation.

As it is shown in Example 2, two PEG/Pi aqueous two-phase systems composed of:

PEG 1500: 12% w/w PEG, 20% w/w Pi supplemented with 10% w/w NaCl, and

PEG 3000: 12% w/w PEG, 20% w/w Pi supplemented with 3.5% w/w NaCl were selected as the systems with the highest selectivity of SOD over native microalga total proteins. Under these conditions, sufficient purification (2-4 fold) with high recovery (>80%) was achieved for SOD activity at the bottom phosphate (Pi) phase. In addition, those systems allow removal of unwanted low molecular weight compounds, such as chlorophylls and polyphenols. The SOD/phosphate phase exhibits high thermostability at 50° C. and 60° C.

The different phases (PEG and Pi) can be separated by pipetting the top (PEG) and bottom (Pi) phases carefully to avoid cross contamination.

Therefore, in a particular embodiment, the PEG phase of the PEG/Pi aqueous two-phase system comprises PEG of an average molecular weight comprised between about 1,500 Da and about 3,000 Da, preferably about 3,000 Da.

In another particular embodiment, the Pi phase of the PEG/Pi aqueous two-phase system comprises a $KH_2PO_4$ buffer pH 7 containing 10% NaCl (w/w).

According to the SOD purification method of the invention, a protein extract enriched in SOD from a biomass of a microalga of the species *T. chuii* in the phosphate aqueous fraction is obtained.

Said protein extract enriched in SOD from a biomass of a microalga of the species *T. chuii* obtained according to the purification method of the invention, hereinafter referred to as the "protein extract enriched in SOD of the invention", constitutes an additional inventive aspect of the present invention.

The SOD activity in the protein extract enriched in SOD of the invention can vary broadly; nevertheless, in a particular embodiment, the SOD activity in the protein extract enriched in SOD of the invention is equal to or higher than 50%, usually equal to or higher than 60%, normally equal to or higher than 70%, preferably equal to or higher than 80%, even more preferably equal to or higher than 90%.

Due to the presence of SOD activity in the protein extract enriched in SOD of the invention, said protein extract can be used in the same uses and applications as those previously mentioned in connection with the biomass of *T. chuii* enriched in SOD of the invention.

Uses of the Biomass of *T. chuii* Enriched in SOD,
of the Brine-Treated Biomass of a Microalga of the
Species *T. chuii* Enriched in SOD and of the
Protein Extract Enriched in SOD Due to the presence of SOD activity in the biomass of *T. chuii* enriched in SOD of the invention, said biomass of *T. chuii* enriched in SOD of the invention shows antioxidant and/or anti-inflammatory activity and can be used in the food, cosmetic and/or pharmaceutical industries as a nutritional active ingredient, cosmetic active ingredient or pharmaceutical active ingredient. Similarly, the stabilized biomass of *T. chuii* enriched in SOD of the invention (i.e., the dehydrated biomass of a microalga of the species *T. chuii* enriched in SOD and the brine-treated biomass of a microalga of the species *T. chuii* enriched in SOD) as well as the protein extract enriched in SOD of the invention, show antioxidant and/or anti-inflammatory activity and can be used in the food, cosmetic and/or pharmaceutical industries as a supplement of a foodstuff or as a cosmetic or pharmaceutical active ingredient.

For simplicity, the generic term "active product of the invention" will refer to the biomass of *T. chuii* enriched in SOD of the invention, the stabilized biomass of *T. chuii* enriched in SOD of the invention and to the protein extract enriched in SOD of the invention, unless otherwise indicated.

Therefore, in an aspect, the invention relates to the use of the active product of the invention as a supplement of a foodstuff.

Thus, in another aspect, the invention relates to a foodstuff comprising the active product of the invention. As used herein, the term "foodstuff" refers to any substance or product of any nature, solid or liquid, natural or processed which due to its characteristics, applications, components, preparation and state of preservation, can usually or ideally be used for some of the following purposes: a) as normal nutrition for human beings or animals or as pleasurable foods; or b) as dietetic products, in especial cases of human or animal food; thus, the definition broadly covers all the natural materials and finished products of any origin which, separately or conveniently mixed with one another, are suitable in the diet of human beings or animals. A ready-to-eat foodstuff is that which does not need to be diluted by means of an aqueous solution suitable for consumption for example. In principle, the ingredients present in a ready-to-eat foodstuff are balanced and there is no need to add additional ingredients to the foodstuff to make it ready to eat, such considered by a person skilled in the art. A concentrated foodstuff is that in which one or more ingredients are present at a higher concentration than in a ready-to-eat foodstuff, therefore for use it is necessary to dilute it by means of an aqueous solution suitable for consumption for example. Non-limiting, illustrative examples of foods provided by this invention include dairy products as milk, yogurts, margarines; drinks as juices and sport drinks; foods like biscuits, breads, cereals, pasta, sauces, etc.

In a particular embodiment, the foodstuff comprises between 0.001% and 99.998% by weight of the active product of the invention.

The foodstuff comprising the active product of the invention can be prepared easily by adding the active product of the invention to the foodstuff and mixing the resulting mixture.

In another aspect, the invention relates to a nutraceutical product comprising the active product of the invention. As used herein, the term "nutraceutical", which derives from the terms "nutrition" and "pharmaceutical", refers to a product made from a food but which is found in a capsule, powder or other pharmaceutical forms not usually associated with food and having the beneficial properties for the treatment and/or prevention of diseases. Therefore, the term "nutraceutical product" includes isolated or purified food products as well as additives or food supplements which are generally presented in dosage forms normally used orally, for example, capsules, tablets, sachets, drinkable phials, etc.; such products provide a physiological benefit or protection against diseases. If desired, the nutraceutical product provided by the invention can contain, in addition to the active product of the invention, one or more nutraceuticals (products or substances associated with disease prevention or reduction), for example, flavonoids, omega-3 fatty acids, etc., and/or one or more prebiotics (non-digestible food ingredients which stimulate probiotic activity and/or growth); for example, oligofructose, pectin, inulin, galacto-oligosaccharides, lactulose, human milk oligosaccharides, dietary fiber, etc.

In a particular embodiment, the nutraceutical product provided by the present invention comprises the active product of the invention and an acceptable oral carrier therefor. In another particular embodiment, the nutraceutical composition provided by the present invention comprises between 0.001% and 99.998% by weight of the active product of the invention. In another particular embodiment, the active product in the nutraceutical composition provided by the present invention is contained in an aqueous phase of said composition. In another particular embodiment, the nutraceutical composition provided by the present invention comprises an oil-in-water emulsion.

In another aspect, the invention relates to the use of the active product of the invention as a food supplement. As used herein, the term "food supplement", refers to concentrated sources of nutrients or other substances with a nutritional or physiological effect whose purpose is to supplement the normal diet. They are marketed 'in dose' form i.e. as pills, tablets, capsules, liquids in measured doses, etc.

In another aspect, the invention relates to the use of the active product of the invention as a cosmetic.

Thus, in another aspect, the invention relates to a cosmetic composition comprising the active product of the invention together with a cosmetically acceptable vehicle. As used herein, the term "cosmetic composition" or "personal care composition" refers to a composition suitable for use in personal hygiene of human beings or animals, or in order to enhance the natural beauty or change the body appearance without affecting the structure or functions of the human or animal body, comprising one or more products providing such effects. If desired, the cosmetic composition provided by the invention can contain, in addition to the active product of the invention, one or more cosmetics or cosmetic products, i.e., substances or mixtures intended to be placed in contact with the external parts of the human or animal body (e.g., epidermis, hair system, nails, lips, etc.) or with the teeth and the buccal mucosa, for the exclusive or main purpose of cleaning them, perfuming them, changing their appearance, protecting them, keeping them in good condition or correcting body odors. Illustrative examples of cosmetic products include the products contained in the INCI (International Nomenclature of Cosmetic Ingredients) list. Cosmetic or personal care compositions include products such as balms, pads, pomades, creams, etc.

In a particular embodiment, the cosmetic composition provided by the present invention comprises an active product of the invention and an acceptable oral or topical carrier therefor.

In another particular embodiment, the cosmetic composition provided by the present invention comprises between 0.001% and 99.998% by weight of the active product of the invention.

The cosmetic composition comprising the active product of the invention can be prepared easily by adding and mixing the different ingredients of said cosmetic composition.

The cosmetic composition provided by the present invention can be used in the prevention, amelioration, or treatment of damage of mammalian skin, for the hydration of the skin or as an anti-aging agent.

In another aspect, the invention relates to the use of the active product of the invention as an antioxidant.

In another aspect, the invention relates to the use of the active product of the invention as a medicament, or, alternatively expressed, to the active product of the invention for use in medicine.

Thus, in another aspect, the invention relates to a pharmaceutical composition comprising an active product of the invention together with a pharmaceutically acceptable vehicle, for example an acceptable oral or topical carrier. Information about excipients suitable for the formulation of pharmaceutical compositions as well as about the production of said pharmaceutical compositions can be found in the book "Tratado de Farmacia Galénica", by C. Fauli i Trillo, $10^{th}$ Edition, 1993, Luzán 5, S. A. de Ediciones.

In a particular embodiment, the pharmaceutical composition provided by the present invention comprises between 0.001% and 99.998% by weight of the active product of the invention.

The pharmaceutical composition comprising the active product of the invention can be prepared easily by adding and mixing the different ingredients of said pharmaceutical composition. Information about carriers or excipients suitable for the formulation of pharmaceutical compositions as well as about the production of said pharmaceutical compositions can be found in the book "Tratado de Farmacia Galénica", by C. Fauli i Trillo, $10^{th}$ Edition, 1993, Luzán 5, S. A. de Ediciones.

In another aspect, the invention relates to the active product of the invention for use in the prevention and/or treatment of a disease or condition characterised by an oxidative stress and/or by an inflammatory activity, or in improving tolerance to radiation therapy; or, expressed in an alternative way, the invention also relates to the use of the active product of the invention in the manufacture of a pharmaceutical composition for the prevention and/or treatment of a disease or condition characterised by an oxidative stress and/or by an inflammatory activity, or in improving tolerance to radiation therapy.

As used herein, the expression "disease or condition characterised by an oxidative stress activity" relates to a disease or condition wherein an oxidative stress is involved. Oxidative stress reflects an imbalance between the systemic manifestation of reactive oxygen species and a biological system's ability to readily detoxify the reactive intermediates or to repair the resulting damage. Disturbances in the normal redox state of cells can cause toxic effects through the production of peroxides and free radicals that damage all components of the cell, including proteins, lipids and DNA. Further, some reactive oxidative species act as cellular messengers in redox signaling; thus, oxidative stress can cause disruptions in normal mechanisms of cellular signaling. In humans, oxidative stress is thought to be involved in the development of cancer; neurodegenerative diseases, such as, for example, Parkinson's disease, Alzheimer's disease, Lou Gehrig's disease, Huntington's disease and Multiple Sclerosis; cardiovascular diseases, such as, for example, atherosclerosis, heart failure, hypertension, myocardial infarction, etc.; as well as in other diseases such as, for example, fragile X syndrome, Sickle Cell Disease, lichen planus, vitiligo, autism, infection and chronic fatigue syndrome.

As used herein, the expression "disease or condition characterised by an inflammatory activity" relates to a disease or condition wherein inflammation is involved. Inflammation is a protective immunovascular response that involves immune cells, blood vessels, and molecular mediators. The purpose of inflammation is to eliminate the initial cause of cell injury, clear out necrotic cells and tissues damaged from the original insult and the inflammatory process, and to initiate tissue repair. Inflammatory abnormalities are a large group of disorders that underlie a vast variety of human diseases. The immune system is often involved with inflammatory disorders, demonstrated in both allergic reactions and some myopathies, with many immune system disorders resulting in abnormal inflammation. Non-immune diseases with etiological origins in inflammatory processes include cancer, atherosclerosis, and ischaemic heart disease (myocardial ischemia). Illustrative, non-limitative, examples of disorders associated with inflammation include: acne vulgaris, acute kidney injury, asthma, autoimmune diseases, autoinflammatory diseases, Behçet's disease, celiac disease, chronic prostatitis, colitis, Crohn's disease, dermatitis, diabetic retinopathy, emphysema, fibrosis, glomerulonefphritis, hypersensitivities (allergies), inflammatory bowel diseases, interstitial cystitis, myopathies, pelvic inflammatory disease, Peyronie's disease, ischemia-reperfusion injury, rheumathoid arthritis, sarcoidosis, sclerosis, skin lesions, systemic lupus erythematosus, transplant rejection, urinary tract inflammatory disease, vasculitis, etc.

In a particular embodiment, the disease or condition characterised by an oxidative stress or inflammatory activity is selected from the group consisting of cancer, Parkinson's disease, Alzheimer's disease, Lou Gehrig's disease, Huntington's disease, Multiple Sclerosis, atherosclerosis, heart failure, hypertension, myocardial infarction, fragile X syndrome, Sickle Cell Disease, lichen planus, vitiligo, autism, infection, chronic fatigue syndrome, ischaemic heart disease, acne vulgaris, acute kidney injury, asthma, autoimmune diseases, autoinflammatory diseases, Behçet's disease, celiac disease, chronic prostatitis, colitis, Crohn's disease, dermatitis, diabetic retinopathy, emphysema, fibrosis, glomerulonefphritis, hypersensitivities (allergies), inflammatory bowel diseases, interstitial cystitis, myopathies, pelvic inflammatory disease, Peyronie's disease, ischemia-reperfusion injury, rheumathoid arthritis, sarcoidosis, sclerosis, skin lesions, systemic lupus erythematosus, transplant rejection, urinary tract inflammatory disease and vasculitis.

The invention also relates to a method for the prevention and/or treatment of a disease or condition characterised by an oxidative stress and/or by an inflammatory activity, or in improving tolerance to radiation therapy, which comprises administering to a subject in need thereof a therapeutically effective amount of an active product of the invention.

As used herein, the term "subject" includes any mammal animal including human being.

The particulars of the active product of the invention have already been defined above and are incorporated herein by reference.

Use of a Brine Solution Rich in Magnesium

In another aspect, the invention relates to the use of a brine comprising between 10 and 18 g/L total sulphur (S), between 40 and 55 g/L sulphate ($SO_4^{2-}$), between 60 and 1,500 mg/L calcium ($Ca^{2+}$), between 52 and 70 g/L magnesium ($Mg^{2+}$), between 15 and 20 g/L potassium ($K^+$), between 9 and 20 g/L potassium ($Na^+$), between 115 and 180 g/L chloride ($Cl^-$) and having a density between 1.25 and 1.30 g/ml at 20° C. as a stabiliser of SOD comprised in a biomass of a microalga containing SOD.

The biomass of any microalga containing SOD activity can be stabilised with said brine solution rich in magnesium; nevertheless, in a particular embodiment, said biomass of a microalga containing SOD is the biomass of T. chuii enriched in SOD of the invention.

In another aspect, the invention relates to a biomass of T. chuii enriched in SOD of the invention characterised in that the SOD is stabilised with a brine, wherein the brine comprises between 10 and 18 g/L total sulphur (S), and between 40 and 55 g/L sulphate ($SO_4^{2-}$), and between 60 and 1,500 mg/L calcium ($Ca^{2+}$), and between 52 and 70 g/L magnesium ($Mg^{2+}$), and between 15 and 20 g/L potassium ($K^+$), and between 9 and 20 g/L potassium ($Na^+$), and between 115 and 180 g/L chloride ($Cl^-$) and having a density between 1.25 and 1.30 g/ml at 20° C.

In a particular embodiment, the brine is added to a biomass of a microalga containing SOD which is substantially free of culture medium, in such a way that the resulting product, i.e., the biomass of a microalga of the species T. chuii enriched in SOD wherein SOD is stabilised with a brine, has essentially the same composition as the composition of the brine, i.e., the biomass of a microalga of the species T. chuii enriched in SOD characterised in that the SOD is stabilised with a brine comprises between 10 and 18 g/L total sulphur (S), and between 40 and 55 g/L sulphate ($SO_4^{2-}$), and between 60 and 1,500 mg/L calcium ($Ca^{2+}$), and between 52 and 70 g/L magnesium ($Mg^{2+}$), and between 15 and 20 g/L potassium ($K^+$), and between 9 and 20 g/L potassium ($Na^+$), and between 115 and 180 g/L chloride ($Cl^-$) and having a density between 1.25 and 1.30 g/ml at 20° C.

In another particular embodiment, the brine is added to a biomass of a microalga containing SOD comprising a certain volume of culture medium, in such a way that the product, i.e., the biomass of a microalga of the species T. chuii enriched in SOD wherein SOD is stabilised with a brine, has a composition that essentially differs from the composition of the brine. The composition of said resulting product will depend on the relative amounts of brine and biomass that are mixed to obtain said product. In a particular embodiment, the ration between the brine and the biomass of a microalga containing SOD is from about 1000:1 to about 1:1000, from about 100:1 to about 1:100, from about 50:1 to about 1:50, from about 25:1 to about 1:25; from about 10:1 to about 1:10; from about 5:1 to about 1:5, about 1:1.

The following examples illustrate the invention and must not be considered as limiting the same.

EXAMPLE 1

Production of SOD in Different Species of Microalgae Under Different Culture Systems and Conditions This assay was performed to study the production of SOD in different species of microalgae under different culture systems and conditions. To that end, a total of 11 microalga strains were tested under different abiotic stress conditions in different culturing systems including indoor and outdoor cultures to see how these affect the SOD activity of the different strains. As it is shown below, *Tetraselmis chuii* was found to have the highest SOD activity in all the abiotic conditions tested, although the highest activity was obtained under nitrogen starvation.

1. Materials and Methods

1.1. Microalga Cultures

The algae *Chlorella vulgaris*, *Chlorella pyrenoidosa*, *Tetraselmis suecica*, *Tetraselmis chuii*, *Tetraselmis* sp., *Nannochloropsis gaditana*, *Phaeodactylum tricornutum*, *Isochrysis galbana* (Clon T-ISO), *Porphyridium cruentum*, and *Scenedesmus obliquous* were obtained from the Microalga Culture Collection of Fitoplancton Marino, S. L.

*T. suecica*, *T. chuii*, *Tetraselmis* sp., *N. gaditana*, *I. galbana* (Clon T-ISO) and *P. cruentum* were cultured in F/2 culture medium [Guilard R. R. L. & Ryther, J. H. 1962. "Studies of marine planktonic diatoms. I. Cyclotela nana Hustedt and Detonula confervaceae (Cleve) Gran." Can. J. Microbiol. 8, 229-239]. *P. tricornutum* was cultured in F/2+Si culture medium [Guilard & Ryther, 1962, cited supra]. *Ch. vulgaris*, *Ch. pyrenoidosa* and *S. obliquous* were cultured with Bold Basal medium with vitamins [Bischoff, H. W. & Bold, H. C. 1963. "Phycological Studies IV. Some Soil Algae from Enchanted Rock and Related Algal Species." University of Texas Publication No. 6318, Austin, Tex.; Starr R. C. & Zeikus J. A. 1993. "UTEX—The Culture Collection of Algae at the University of Texas at Austin" J. Phycol. Suppl. 29]. All media were prepared fresh from respective dry chemicals.

Starter cultures of 50 mL (in mid-log stage) were inoculated to 800 mL medium in 1,000 mL Erlenmeyer flasks. The Erlenmeyer flasks were placed in a control temperature room at 25±1° C. under continuous cool white fluorescent light of 150 µmol photon $m^{-2}$ $s^{-1}$. The cultures were aerated with approximately 2% $CO_2$ in atmospheric air. Every week, 50 mL of a culture were transferred to a new flask containing fresh medium. These cultures were maintained by sub-culturing every week and were used as inoculum for indoor and outdoor experiments.

1.2. Culture Conditions

The experimental culture conditions were established, maintaining three replicates in each: control condition, which corresponds to the maintenance condition of the stock culture; indoor and outdoor conditions in which cultures were subjected to high redox conditions, high temperature conditions, nitrogen starvation conditions and high salinity conditions.

Cultures were operated in fed-batch mode in order to prevent nutrient limitation. Cultures were grown to log phase before the abiotic conditions were applied. Growth rates were monitored by microscopy cell counts. Growth curves (not shown) were constructed to confirm growth stage identification as this depends on the strain that was being cultured.

High redox conditions, in which cultures media were maintained with a redox potential of at least 100 mV, were obtained by the addition of ozone. For small volume cultures, the ozone was generated in the media by an OZAC-PLUS 200 ozone generator with an oxidation/reduction potential (ORP) controller. For big volumes, an Oxicom SLV 250 ozone generator was used wherein the dissolved ozone concentration in the media was controlled by measuring the ORP continuously by an mV 600 ORP Digital Controller from Hannah Instruments.

High temperature conditions, in which cultures were maintained, were obtained at a temperature higher than 28° C. For indoor cultures, the temperature of the culturing room was set above this temperature. For outdoor cultures, the cultures had to be done during the Spring and Summer periods, i.e., when temperature was reached naturally by the environmental temperature.

High salinity conditions, in which cultures media were cultured, were obtained by culturing the cultures media at salinity greater than 35 by adding salts to the media. The salinity was measured using a HI 9828 Multiparameter from Hanna instrument.

Nitrogen starvation conditions were encountered by not adding nitrogen to the media and therefore being consumed by the culture. Nitrogen concentration was determined by an AQ2 autoanalizer from Seal.

1.3. Culture Systems

Indoor cultures were performed in 5 L Erlenmeyer flasks. Outdoor cultures were performed in either open or closed systems.

The open systems used were race way ponds. Cultivations were carried out in 6 L and 600 L acrylic open raceway ponds containing 5 L and 500 L, respectively, of culture medium. The cultures were moved using a paddle-wheel rotating at 18 revolutions per minute (rpm). This raceway pond was constructed with a design adopted from previous studies [Radmann, E. M. et al, 2007, Aquaculture 2007, 265: 118-126].

The closed systems used were tubular photobioreactors (PBR) consisting of a pump that drove the culture medium trough a horizontal tubular solar receiver. The total culture volume in the bioreactor was 650 L and 2,000 L.

Both raceway ponds and photobioreactors used pure $CO_2$ injection to control pH in the culture by pH controller and flowmeters. pH was set at 7.8.

Biomass was collected directly from the different cultures centrifuged in a batch centrifuge, at 5,000 rpm for 15 min. The harvested biomass had 80% moisture. The biomass paste was washed with distilled water to remove non-biological material such as mineral salt precipitates. The biomass samples of microalgae to be analysed for SOD activity and for the preparation of the aqueous two-phase system was stabilized either by freeze-drying or by adding the paste to a brine solution rich in magnesium. This brine solution was obtained by sea water evaporation.

1.4. Protein Extraction and Measurement

Protein extraction and SOD extracts were obtained by the addition of 1 mL of extraction buffer (220 mM $KH_2PO_4$ buffer pH 7.8) to 0.1 g of biomass of microalgae. The cells were lysed using ultrasounds for 2 min with 10 seconds intervals (4 cycles of 30 sec each, 20% amplification). The biomass was then centrifuged at 16,000 rpm for 10 min at room temperature and the supernatant collected. The protein concentration was determined by the traditional Bradford method [Bradford M. M. 1976. "A rapid and sensitive method for the quantitation of microgram quantities of protein utilizing the principle of protein-dye binding." Analyt. Biochem. 72, 248-254].

1.5. Enzyme Assay

The SOD activity in all the following experiments was assayed following the inhibition of the rate of reduction of cytochrome c in a coupled system, using xanthine and xanthine oxidase at 216 mM Pi, pH 7.8, as mentioned below [McCord, J. M. and Fridovich, I. (1969) J. Biol. Chem. 244, 6049 6055; Procedure updated from SOP 10-30-6299 and OP SPCYTO01].

Enzymatic Assay of Superoxide Dismutase

The objective of this assay is to standardize a procedure for the enzymatic determination of superoxide dismutase (SOD). This procedure applies to all products that have a specification for superoxide dismutase activity by enzymatic determination.

Definitions

Purified Water=water from a deionizing system, resistivity> or =18MΩ·cm@25° C.

Unit Definition—One unit will inhibit the rate of reduction of cytochrome c by 50% in a coupled system, using xanthine and xanthine oxidase at pH 7.8 at 25° C. in a 3.0 mL reaction volume. The xanthine oxidase concentration should produce an initial (uninhibited) $\Delta A_{550\ nm}$ of 0.025+/−0.005 per minute.

XOD—Xanthine Oxidase
SOD—Superoxide Dismutase
O2⁻·—Superoxide Radical

Discussion

The superoxide radical is produced enzymatically by the reaction catalyzed by Xanthine Oxidase:

Oxidised cytochrome c is reduced by the superoxide radical. The rate of reduction is followed spectrophotometrically at 550 nm:

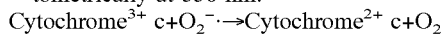

Superoxide dismutase inhibits the reduction of cytochrome c by competing for the superoxide radical:

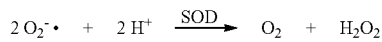

Procedure

Conditions: T=25° C., pH=7.8, $A_{550\ nm}$, Light path=1 cm

Method: Continuous Spectrophotometric Rate Determination Reagents:

A) 216 mM Potassium Phosphate Buffer, pH 7.8 at 25° C. (Buffer) [prepare a 49.3 mg/mL solution of potassium phosphate dibasic trihydrate, Sigma-Aldrich Product Number, P5504 in purified water; adjust the pH to 7.8 at 25° C. with 1 M KOH or 1 M HCl];

B) 10.7 mM Ethylenediaminetetraacetic Acid Solution (EDTA) [prepare 4.0 mg/mL solution of Ethylenediaminetetraacetic acid disodium salt dihydrate, Sigma-Aldrich Stock Number, ED2SS in purified water];

C) 1.1 mM Cytochrome C Solution (Cyt C) [prepare a 14.6 mg/ml solution of Cytochrome C, Sigma-Aldrich Product Number, C7752 in purified water];

D) 0.108 mM Xanthine Solution (Xanthine) [dissolve 1.64 mg of Xanthine, Sigma-Aldrich Product Number, X0626 in 90 mL of purified water; with stirring, add small amounts of 1N KOH until all of the xanthine has dissolved; quantitatively transfer the solution to a 100 mL volumetric flask and qs to 100 mL with purified water];

E) Xanthine Oxidase Enzyme Solution (XOD) [prepare a solution containing approximately 5 units/mL of xanthine oxidase, Sigma-Aldrich Product Number, X1875 in cold purified water. Place on ice; immediately before use, prepare a solution in cold purified water containing 0.05 units/mL of xanthine oxidase using xanthine oxidase, Sigma-Aldrich Product Number, X1875. This concentration may need to be adjusted to meet the requirements of the assay; and F) Superoxide Dismutase Enzyme Solution [immediately before use, prepare a solution containing 10 units/mL of superoxide dismutase in cold purified water].

Assay Procedure

Prepare a reaction cocktail by pipetting (in milliliters) the following reagents into a suitable container:

| | |
|---|---|
| Purified Water | 23.0 |
| Reagent A (Buffer) | 25.0 |
| Reagent B (EDTA) | 1.0 |
| Reagent C (CytoC) | 1.0 |
| Reagent D (Xanthine) | 50.0 |

Mix to obtain a cocktail ("G") and adjust the pH to 7.8 at 25° C. with 1 M HCl or 1 M KOH if necessary.

Xanthine Oxidase Check:

Pipette the following (in mL) into suitable cuvettes:

| | Blank | XOD |
|---|---|---|
| Reagent G (Cocktail) | 2.80 | 2.80 |

Equilibrate to 25° C. using a suitably thermostated spectrophotometer.

Monitor the Absorbance at 550 nm until constant, then add:

| | | |
|---|---|---|
| Purified Water | 0.20 | 0.10 |
| Reagent E (XOD) | — | 0.10 |

Mix by inversion and record the increase in absorbance at 550 nm for approximately 5 minutes. The change in absorbance for the uninhibited versus the blank should be 0.025+/−0.005 for this reaction. If it is not, adjust the concentration of Reagent E (XOD) and repeat the xanthine oxidase check.

Pipette (in milliliters) the following reagents into suitable cuvettes:

| | Blank | Uninhibited | Test-1 | Test-2 | Test-3 |
|---|---|---|---|---|---|
| Reagent G (Cocktail) | 2.80 | 2.80 | 2.80 | 2.80 | 2.80 |
| Purified water | 0.20 | 0.10 | — | 0.01 | 0.02 |
| Reagent F (SOD) | — | — | 0.10 | 0.09 | 0.08 |

Equilibrate to 25° C. using a suitably thermostated spectrophotometer.

Monitor the Absorbance at 550 nm until constant, then add:

| | | | | | |
|---|---|---|---|---|---|
| Reagent E (XOD) | — | 0.10 | 0.10 | 0.10 | 0.10 |

Mix by inversion and record the increase in absorbance at 550 nm for approximately 5 minutes. Obtain the fastest linear rate over a one minute interval for the uninhibited reaction. Using this time interval, obtain the rates for each Test and Blank.

The $\Delta A_{550\ nm}$ for each inhibited test should fall within 40-60% of the uninhibited rate. Any value outside this range is considered invalid.

Calculations

| 7.5.1 | Percent Inhibition | $(\Delta A_{550nm}/\min \text{Uninhibited} - \Delta A_{550nm}/\min \text{Inhibited}) \times (100)$ |
| --- | --- | --- |
| | | $(\Delta A_{550nm}/\min \text{Uninhibited} - \Delta A_{550nm}/\min \text{Blank})$ |
| | Units/ml Enzyme: | (Percent Inhibition) $(DF)/(50\%)(0.10)$ |

DF=Dilution Factor
50%=Inhibition of the rate of cytochrome c reduction per the unit definition
0.10=Volume (in mL) of enzyme used in each test Final Assay Concentration In a 3.00 ml reaction mix, the final concentrations are 50 mM potassium phosphate, 0.1 mM ethylenediaminetetraacetic acid, 0.01 mM cytochrome c, 0.05 mM xanthine, 0.005 unit xanthine oxidase and 1 unit superoxide dismutase.

Definitions:
a)

$$\text{Yield (\%)} = \frac{\text{Total Enzyme Activity in a Purified fraction}}{\text{Total Enzyme Activity in the Crude Extract}} \times 100$$

b) The specific activity of an enzyme is defined as:

Specific Activity (U/mg)=Activity (Units)/Protein (mg)

c)

$$\text{Enzyme Purity} = \frac{\text{Quantity of the desired enzyme (protein)}}{\text{Quantity of total protein}}$$

The specific activity, the Fold-purification and the % yield for each purification step was compared to the initial starting crude extract. Enzyme purity was measured using the parameter Fold-purification. Fold-purification is a measure of how much more pure is the target protein (i.e., SOD) after a purification step in comparison to the crude extract. Fold-purification can be calculated by dividing the Specific Activity (U/mg protein) of the purified step by the Specific Activity (U/mg protein) of crude extract.

2. Results

The productivity of SOD of the different strains mentioned above was tested under the different abiotic conditions and systems shown in Table 1.

TABLE 1

Description of the different treatments used in the culture of 11 microalga strains
Treatment Indoor conditions
  Standard conditions
  RedOx > 100 mV (reactive oxygen)
  High temperature
  Nitrogen starvation
  High salinity
Outdoor conditions
  Open systems TABLE 1-continued Description of the different treatments used in the culture of 11 microalga strains
Treatment Standard conditions
  RedOx > 100 mV (reactive oxygen)
  High temperature
  Nitrogen starvation
  High salinity
Closed systems
  Standard conditions
  RedOx > 100 mV (reactive oxygen)
  High temperature
  Nitrogen starvation
  High salinity The average production of the different strains tested under standard conditions or under abiotic stress did not show significant increases on the SOD production compared to that obtained by the microalga *T. chuii*, as it is shown in FIG. 1.

All strains, except *T. chuii* and other *Tetraselmis* genus, showed values of SOD activity in the range of 10-60 IU/mg of soluble protein. Some species like *P. tricornutum* and *N. gaditana* showed higher SOD activity, about 100 IU/mg of soluble protein. However, *T. chuii* reached a high SOD activity, namely, about 180 IU/mg of soluble protein under standard conditions which increased to a maximum of SOD activity of 715±15 IU/mg of soluble protein when cultured under the abiotic stress of nitrogen starvation, followed by an SOD activity of 500±12.5 IU/mg of soluble protein when *T. chuii* was cultured under high temperature stress conditions reaching and an SOD activity of 410±18.9 IU/mg of soluble protein when cultured under high salinity stress conditions. Results are shown in FIG. 1. Therefore, *T. chuii* was found to have the highest SOD activity in all the abiotic conditions tested, although the highest activity was obtained under nitrogen starvation. For these reasons, *T. chuii* was selected as microalga for the production of SOD activity in further assays.

There was no significant differences in the results of SOD activity obtained in outdoor cultures for the different culture volumes tested.

EXAMPLE 2

Fractionation and Partial Purification of SOD Activity from the Microalga *T. chuii* Cell Free Extract This study was aimed to develop an economic extraction strategy for the fractionation and partial purification of SOD activity from the microalga *T. chuii* cell free extract. To that end, a polyethyleneglycol/phosphate (PEG/Pi) aqueous two-phase system was developed. Detailed study was carried out to analyze the effect of the PEG molar mass, concentration, pH and ionic composition in the system on the partitioning behavior of SOD activity in the phosphate rich phase. As it is shown below, two PEG/Pi aqueous two-phase systems composed of:

PEG 1500: 12% w/w PEG, 20% w/w Pi supplemented with 10% w/w NaCl, and
PEG 3000: 12% w/w PEG, 20% w/w Pi supplemented with 3.5% w/w NaCl were selected as the systems with the highest selectivity of SOD over native microalga total proteins. Under these conditions, sufficient purification (2-4 fold) with high recovery (>80%) was achieved for SOD at the bottom phosphate phase. In addition, the system allows removal of unwanted low molecular weight compounds, such as chlorophylls and polyphenols. The SOD/phosphate phase exhibits high thermostability at 50° C. and 60° C.

Materials & Methods

Extract

In all cases, microalga *T. chuii* cell free extracts obtained as described in Example 1 were used.

Preparation of Aqueous Two-Phase Systems

Polyethyleneglycol/phosphate (PEG/Pi) aqueous two-phase system were prepared from a 50% (w/w) PEG 1500, 3000 and 6000 stock solutions and from a 40% (w/w) of a potassium phosphate stock solution, pH 7.0. PEG stock solutions were prepared by dissolving the calculated amounts of PEG in deionized water. Potassium phosphate solution was prepared at a proportion of 7:18 monobasic: dibasic by dissolving the calculated amounts of anhydrous monobasic potassium phosphate and anhydrous dibasic potassium phosphate in deionized water, adjusting pH to 7.0 using 1 M sodium hydroxide (NaOH) or 1 M hydrochloric acid (HCl).

Potassium phosphate buffers containing different concentrations of NaCl were prepared by adding, in 25 g of stock potassium phosphate buffer, 0.875 g NaCl (3.5% w/w), 1.75 g NaCl (7% w/w), 2.5 g NaCl (10% w/w). pH was adjusted to 7.0 by using 1 M NaOH or 1 M HCl.

Different system parameters such as the molecular weight of polymer (PEG), salt composition and pH have a great impact on the protein distribution and total yield.

ATPS of 2-100 g of mass containing the required amounts of PEG, salt solution, *T. chuii* cell free extract (supernatant of microalgae, 10% of the total system) and deionized water to balance the total weight were prepared in plastic tubes. ATPS was prepared by mixing the test tubes gently for 1 hour at 22-25° C. To achieve a complete phase separation a low-speed centrifugation at 1,500 rpm for 10 min was performed. Phases were separated by pipetting the top and bottom phases carefully to avoid cross contamination. The volume of each phase was measured and collected.

Various amounts and molecular weights of PEG (1500, 3000 and 6000 Da) as well as of $K_2HPO_4$ using different pH (6.5, 7, 7.5, 8 and 8.5) and at different concentrations of NaCl (0% w/w, 3.5% w/w, 7% w/w and 10% w/w) were added to the extract of microalgae to generate the biphasic system. The amount of $KH_2PO_4$ was constant in all conditions.

Results 2.1. Optimization of ATPS for the Microalga Extract

The distribution of a particular protein depends on its unique physicochemical properties, such as size, surface charge, hydrophobicity, etc. If properly optimized, by carefully adjusting the factors that influence the distribution of proteins (e.g., PEG molecular weight, ionic strength, pH), it can be circumvented many of the shortcomings of centrifugation and ultrafiltration, commonly used at the initial stages of extraction and offer a partially purified and concentrated final product.

Figure 2:
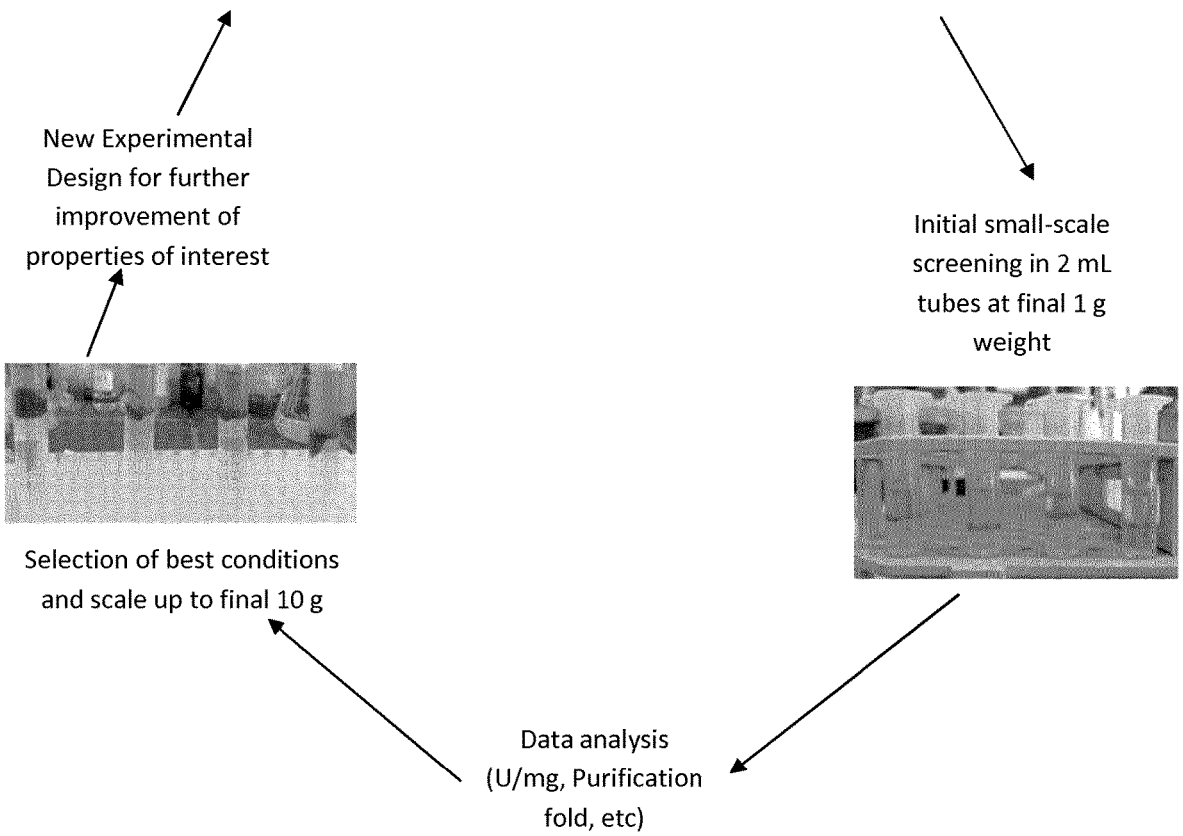
FIG. 2 shows the work flow of the ATPS optimization process.

Considering that the ATPS parameters, such as the molecular weight of the polymer (PEG), salt composition and pH, have a great impact on the protein distribution (Kp, partition coefficient) and the total yield, a factorial experiment was designed and several different conditions were screened (FIG. 2). The tested ranges for both PEG and Pi were 11-20% (w/w). Three PEG molecular weights were tested, namely, 1500, 3000 and 6000. The stock solutions for PEG and Pi were 50% w/w and 40% w/w, pH 7, respectively. Subsequently, the best conditions with respect to the Fold-purification of the SOD in the Pi phase were selected for further improvement (FIG. 2). In all cases *T. chuii* cell free extracts were used. Table 2 shows the initial tested PEG/Pi conditions.

TABLE 2

Initial experimentally tested conditions

| Runs | PEG % w/w | Pi % w/w | PEG (g) | Pi (g) | Sample | ddH$_2$O | Total weight |
|---|---|---|---|---|---|---|---|
| 1 | 15 | 17 | 0.300 | 0.430 | 0.100 | 0.170 | 1 |
| 2 | 20 | 12 | 0.400 | 0.304 | 0.100 | 0.196 | 1 |
| 3 | 12 | 17 | 0.240 | 0.430 | 0.100 | 0.230 | 1 |
| 4 | 19 | 15 | 0.380 | 0.380 | 0.100 | 0.141 | 1 |
| 5 | 16 | 11 | 0.320 | 0.278 | 0.100 | 0.302 | 1 |
| 6 | 16 | 19 | 0.320 | 0.481 | 0.100 | 0.099 | 1 |
| 7 | 18 | 16 | 0.360 | 0.405 | 0.100 | 0.135 | 1 |
| 8 | 11 | 18 | 0.220 | 0.455 | 0.100 | 0.225 | 1 |
| 9 | 17 | 15 | 0.340 | 0.380 | 0.100 | 0.181 | 1 |
| 10 | 12 | 20 | 0.240 | 0.506 | 0.100 | 0.154 | 1 |
| 11 | 18 | 12 | 0.360 | 0.304 | 0.100 | 0.236 | 1 |
| 12 | 15 | 20 | 0.300 | 0.506 | 0.100 | 0.094 | 1 |
| 13 | 11 | 13 | 0.220 | 0.329 | 0.100 | 0.351 | 1 |
| 14 | 13 | 18 | 0.260 | 0.455 | 0.100 | 0.185 | 1 |
| 15 | 17 | 14 | 0.340 | 0.354 | 0.100 | 0.206 | 1 |
| 16 | 20 | 14 | 0.400 | 0.354 | 0.100 | 0.146 | 1 |
| 17 | 14 | 19 | 0.280 | 0.481 | 0.100 | 0.139 | 1 |
| 18 | 13 | 11 | 0.260 | 0.278 | 0.100 | 0.362 | 1 |
| 19 | 19 | 13 | 0.380 | 0.329 | 0.100 | 0.191 | 1 |
| 20 | 14 | 16 | 0.280 | 0.405 | 0.100 | 0.215 | 1 |

Figure 3:
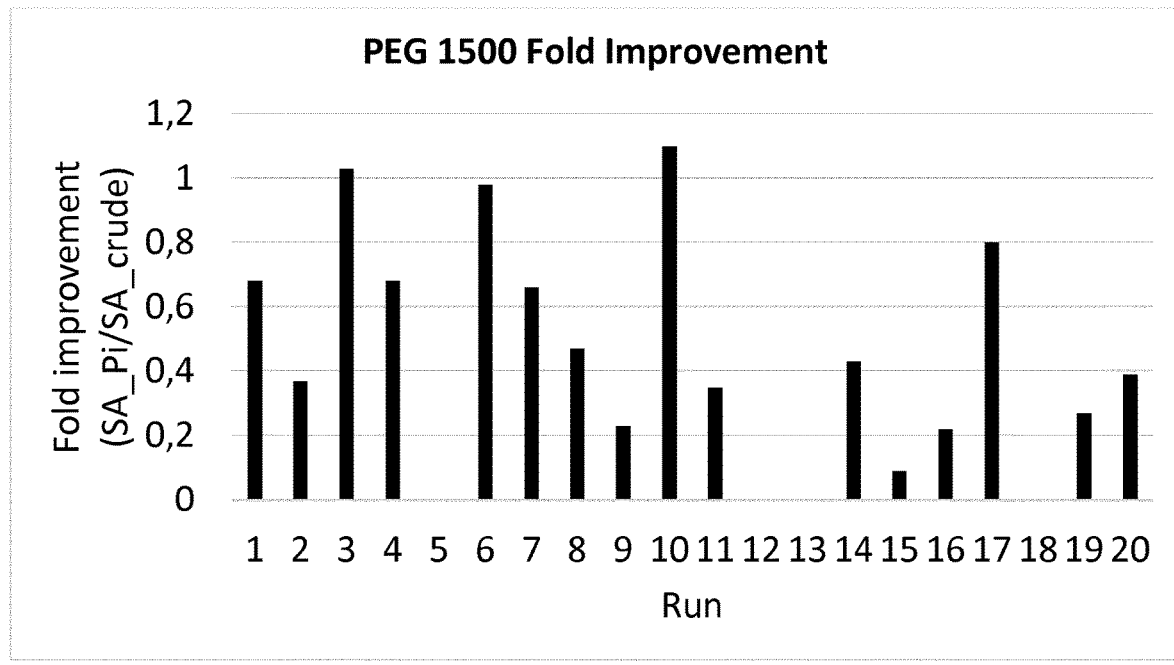
FIG. 3 is a bar diagram showing the effect of different conditions (Table 1) on SOD purification (Fold-purification) using an ATPS composed of PEG 1500.
Figure 4:
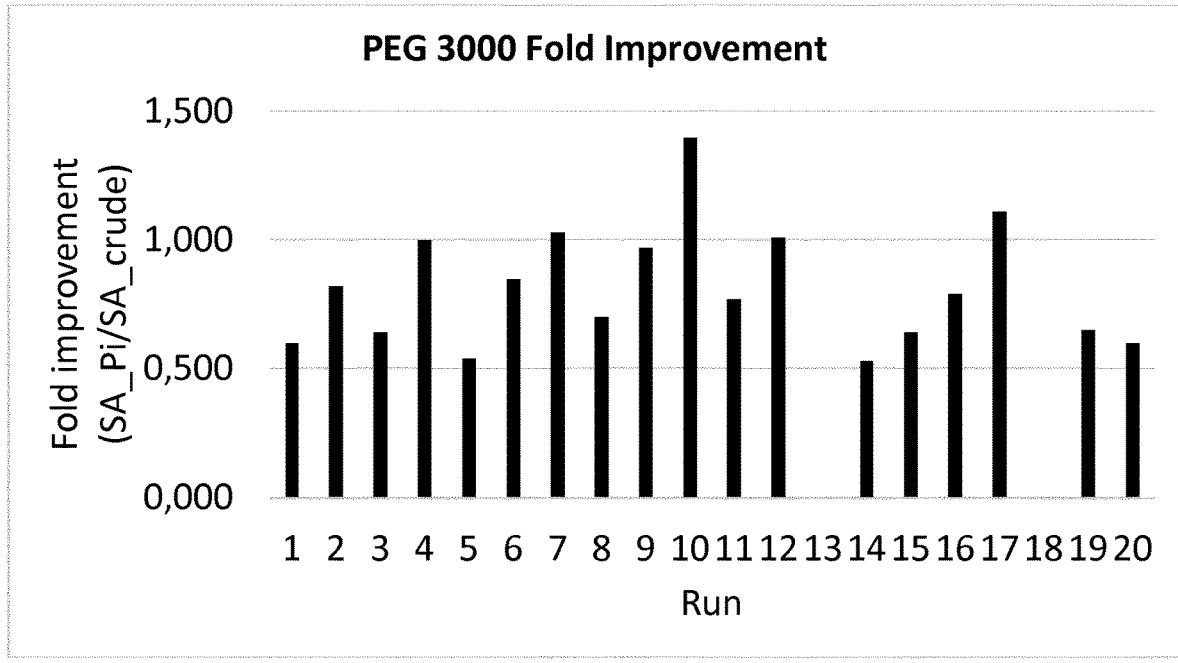
FIG. 4 is a bar diagram showing the effect of different conditions (Table 1) on SOD purification (Fold-purification) using an ATPS composed of PEG 3000.

Those conditions which resulted in the formation of distinct and separated PEG and Pi phases were analyzed for SOD activity in the Pi phase. The results are shown in FIGS. 3 and 4.

Based on the results obtained after the initial screening, the following conditions were selected for further analysis:
a) PEG 1500: Run 10; i.e., 12% w/w PEG, 20% w/w Pi [PEG 1500 (10)]
b) PEG 3000: Run 10; i.e, 12% w/w PEG, 20% w/w Pi [PEG 3000 (10)]

The selected conditions were scaled up to a final weight of 10 g in order to obtain more accurate results, as it is shown in Table 3.

TABLE 3

Scale up of the initial screening's selected conditions

| Run | PEG 1500 (10) | PEG 3000 (10) |
|---|---|---|
| Purification Fold | 2.3 | 2.2 |
| Yield (%) | 70 | 75 |

Figure 5:
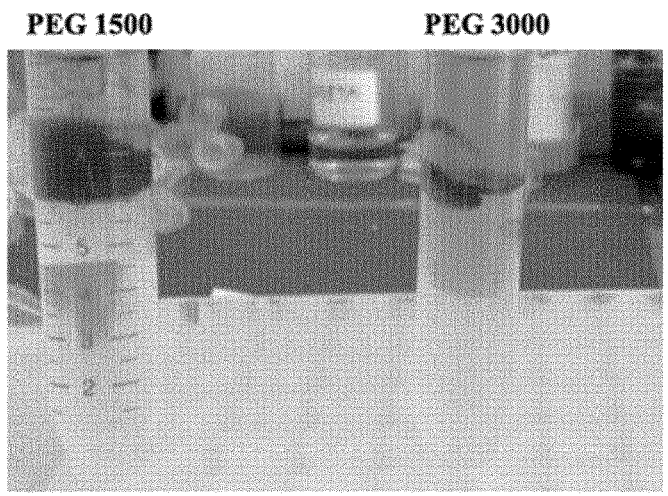
FIG. 5 is a photo showing the final phase separation of the selected conditions after the initial PEG/Pi screening (Example 2), wherein the upper PEG phase, the interface with the cell debris and the lower Pi phase are depicted.

The SOD specific activity (S.A., units/mg protein) improvements for PEG 1500 and PEG 3000 were reproduced. FIG. 5 shows the falcon tubes with the PEG and Pi phase separation of the selected conditions.

The next step included an additional screening step testing different pH and NaCl concentrations. The above selected conditions were used for further improvement of SOD purity. Table 4 shows the tested pH/NaCl conditions.

TABLE 4 pH/NaCl screened conditions

| Run Order | pH | NaCl (% w/w) |
|---|---|---|
| 1 | 6.5 | 7 |
| 2 | 8.5 | 3.5 |
| 3 | 6.5 | 3.5 |
| 4 | 8.5 | 7 |
| 5 | 7.5 | 10 |
| 6 | 6.5 | 3.5 |
| 7 | 6.5 | 10 |
| 8 | 8.5 | 10 |
| 9 | 7.5 | 3.5 |
| 10 | 7.5 | 7 |
| Control 1 (C1) | 7 | 0 |
| Control 2 (C2) | 7 | 3.5 |
| Control 3 (C3) | 7 | 7 |
| Control 4 (C4) | 7 | 10 |
| Control 5 (C5) | 8.5 | 0 |
| Control 6 (C6) | 7.5 | 0 |
| Control 7 (C7) | 6.5 | 0 |

Figure 6:
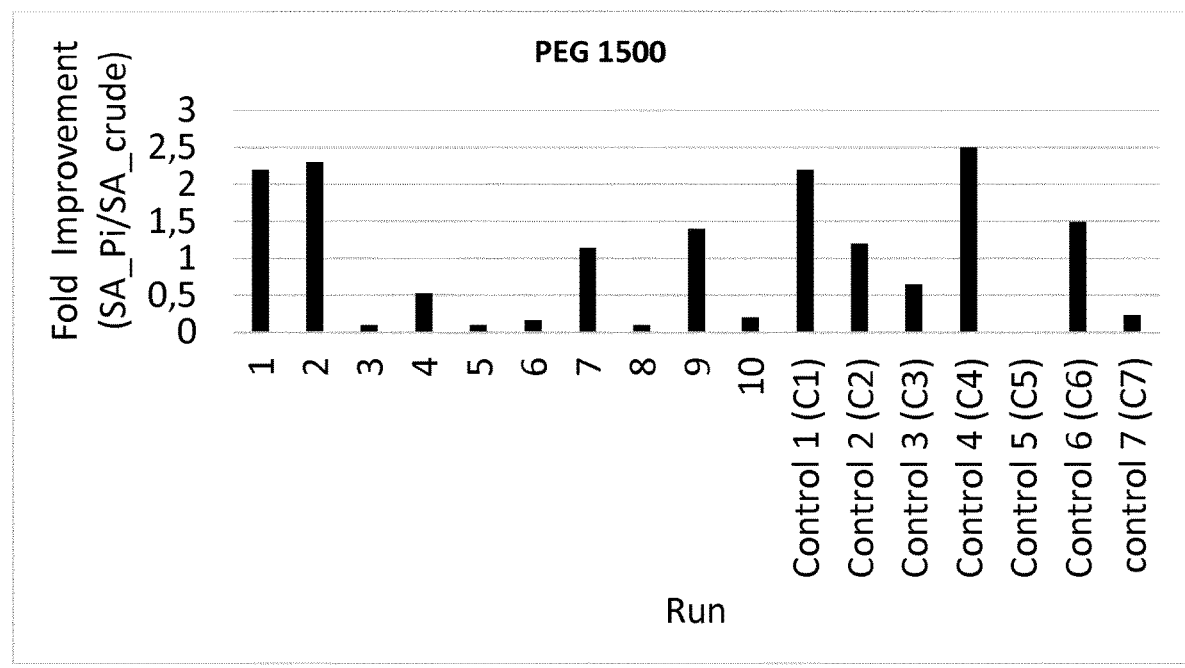
FIG. 6 is a bar diagram showing the Fold-purification of the different pH/NaCl screened conditions (PEG 1500).
Figure 7:
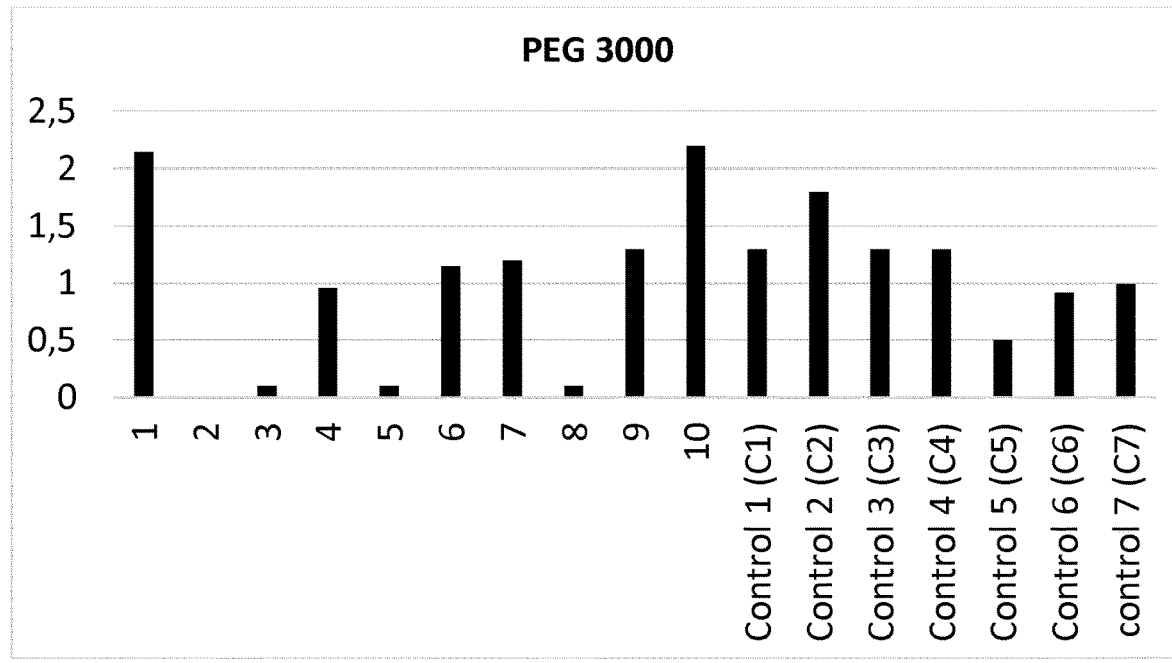
FIG. 7 is a bar diagram showing the Fold-purification of the different pH/NaCl screened conditions (PEG 3000).
Figure 8:
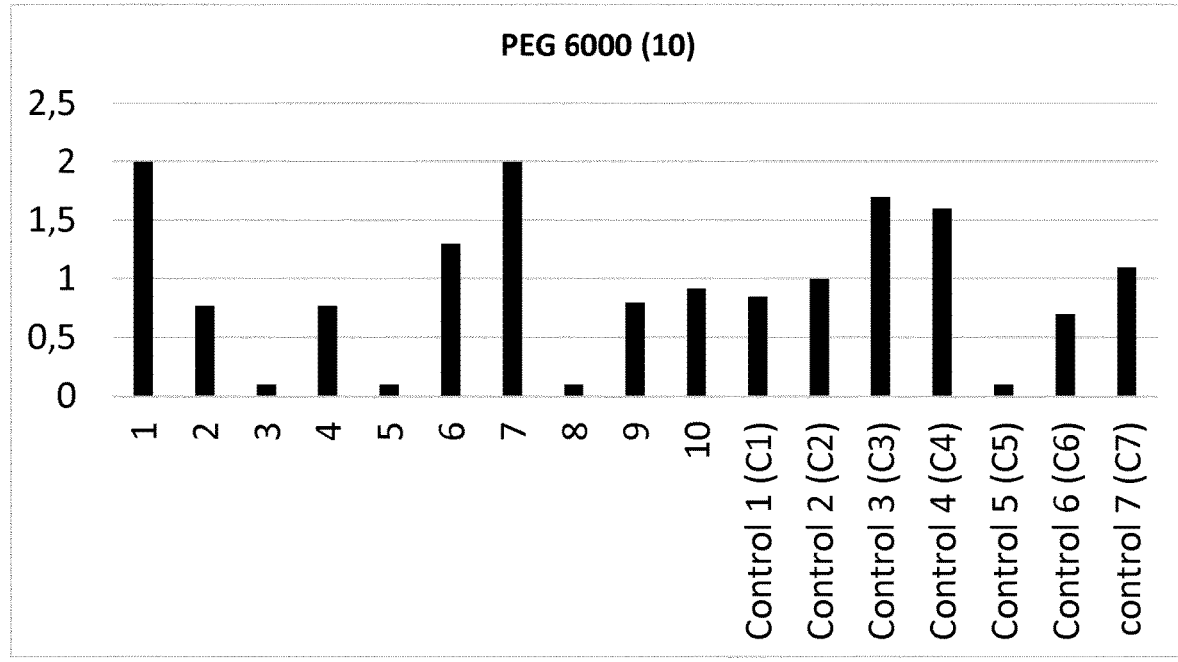
FIG. 8 is a bar diagram showing the Fold-purification of the different pH/NaCl screened conditions (PEG 6000 (10)).

FIGS. 6-8 show the purification improvement of the pH/NaCl screened conditions.

Based on the results above, the following conditions were selected for scaling up:
a) PEG 1500: 1, 2 & C4
b) PEG 3000: 1, 10 & C2
c) PEG 6000 (10): 1, 7 & C3

Figure 9:
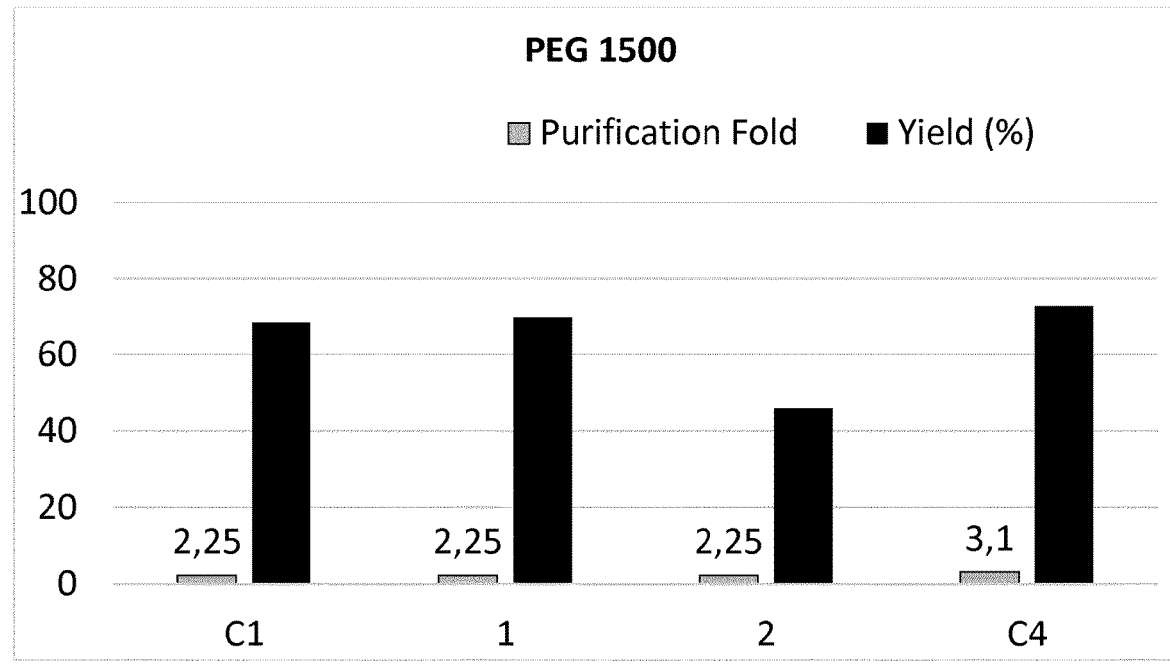
FIG. 9 is a bar diagram showing the Fold-purification and yield of the scaled-up selected conditions (PEG 1500).
Figure 10:
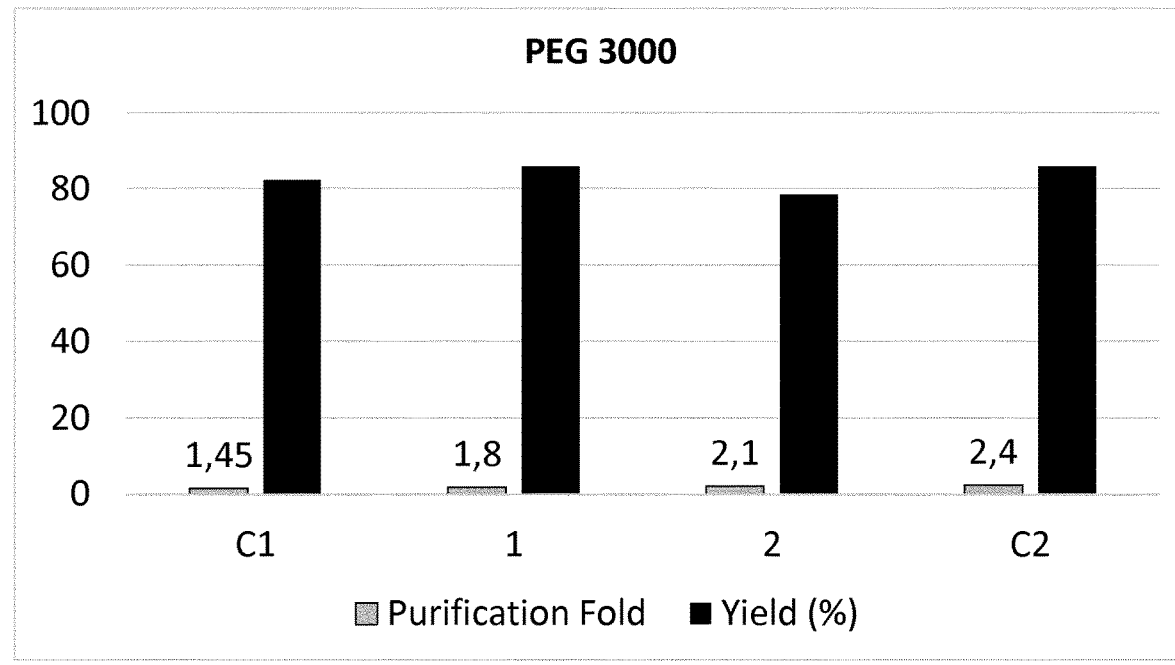
FIG. 10 is a bar diagram showing the Fold-purification and yield of the scaled-up selected conditions (PEG 3000).
Figure 11:
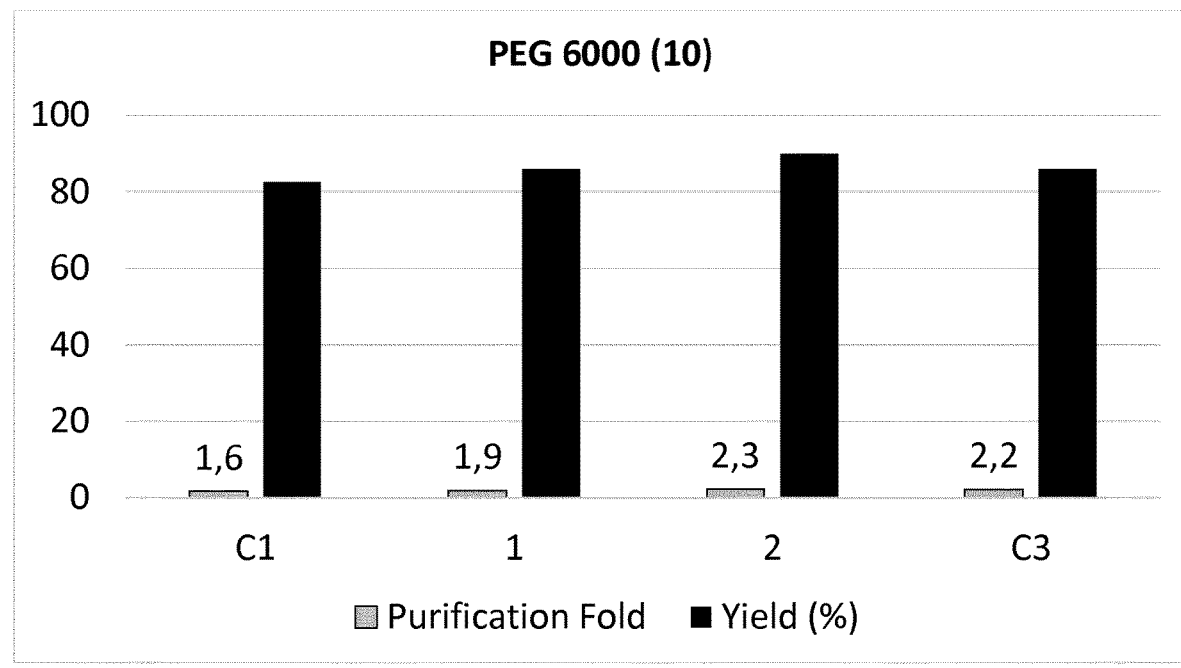
FIG. 11 is a bar diagram showing the Fold-purification and yield of the scaled-up selected conditions (PEG 6000 (10)).

FIGS. 9-11 show the results from the scale-up experiment (10 g) of the selected conditions above.

Figure 12:
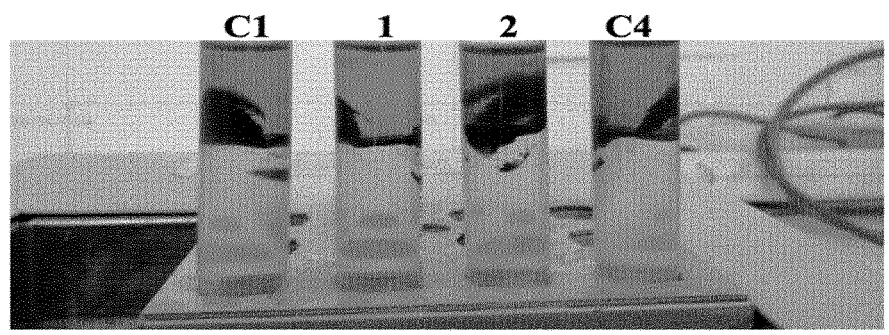
FIG. 12 is a photo showing the PEG 1500 scale-up (10 g) ATPS.
Figure 13:
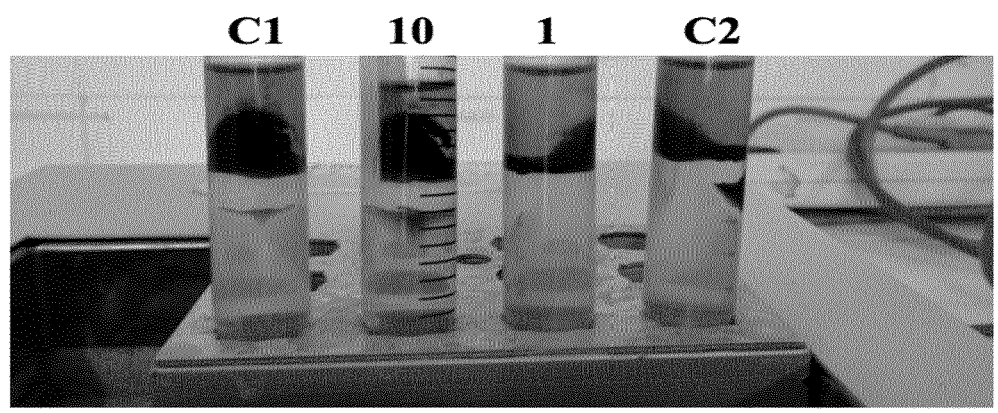
FIG. 13 is a photo showing the PEG 3000 scale-up (10 g) ATPS.
Figure 14:
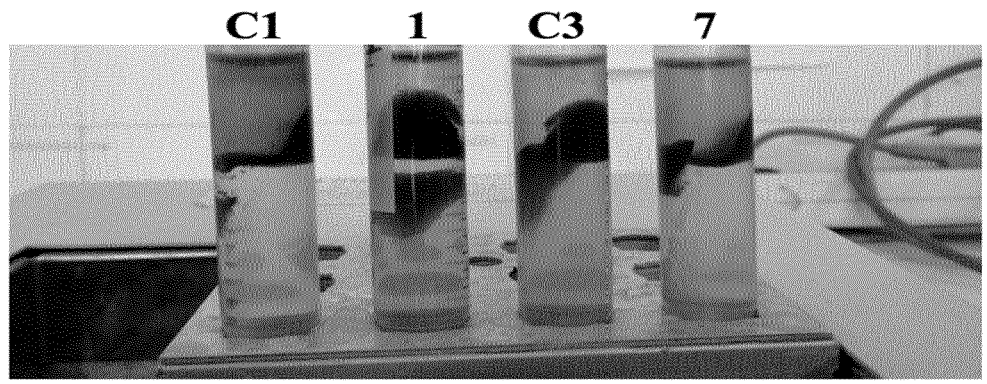
FIG. 14 is a photo showing the PEG 6000 (10) scale-up (10 g) ATPS.

When the best pH/NaCl conditions were tested in final weight of 10 g, all PEG 6000 (10) conditions showed chlorophyll contamination (FIGS. 12,13 and 14) in the Pi phase and, therefore, only the PEG 1500 and PEG 3000 were selected for further improvement.

Ultimately, the final selected conditions after the scale-up trials were the following:
PEG 1500: C4; i.e., 12% w/w PEG, 20% w/w Pi supplemented with 10% w/w NaCl, pH 7
PEG 3000: C2; i.e., 12% w/w PEG, 20% w/w Pi supplemented with 3.5% w/w NaCl, pH 7.

These two PEG/Pi aqueous two-phase systems were selected as the systems with the highest selectivity of SOD over native microalga *T. chuii* total proteins. Under these conditions, sufficient purification (2-4 fold) with high recovery (>80%) was achieved for SOD at the bottom phosphate phase. In addition, both systems allow removal of unwanted low molecular weight compounds, such as chlorophylls and polyphenols.

2.2. Reproducibility of the Optimized ATPS

The reproducibility of the best conditions for the ATPS was investigated. Three independent experiments were performed in three successive days. Phosphate and PEG stock solutions were prepared fresh each time. *T. chuii* cells (0.1 g) were resuspended in 1 mL 220 mM Pi buffer, pH 7.8 and lysed by applying ultrasounds (4 cycles of 30 sec each, 20% amplification). The cells were spun down (16,000×g for 20 minutes) and the supernatant was subjected to ATPS partition. The final weight of the ATPS was 10 g and the final concentrations were:
PEG 1500: 12% w/w PEG, 20% w/w Pi supplemented with 10% w/w NaCl (final concentrations)
PEG 3000: 12% w/w PEG, 20% w/w Pi supplemented with 3.5% w/w NaCl (final concentrations)

Figure 15:
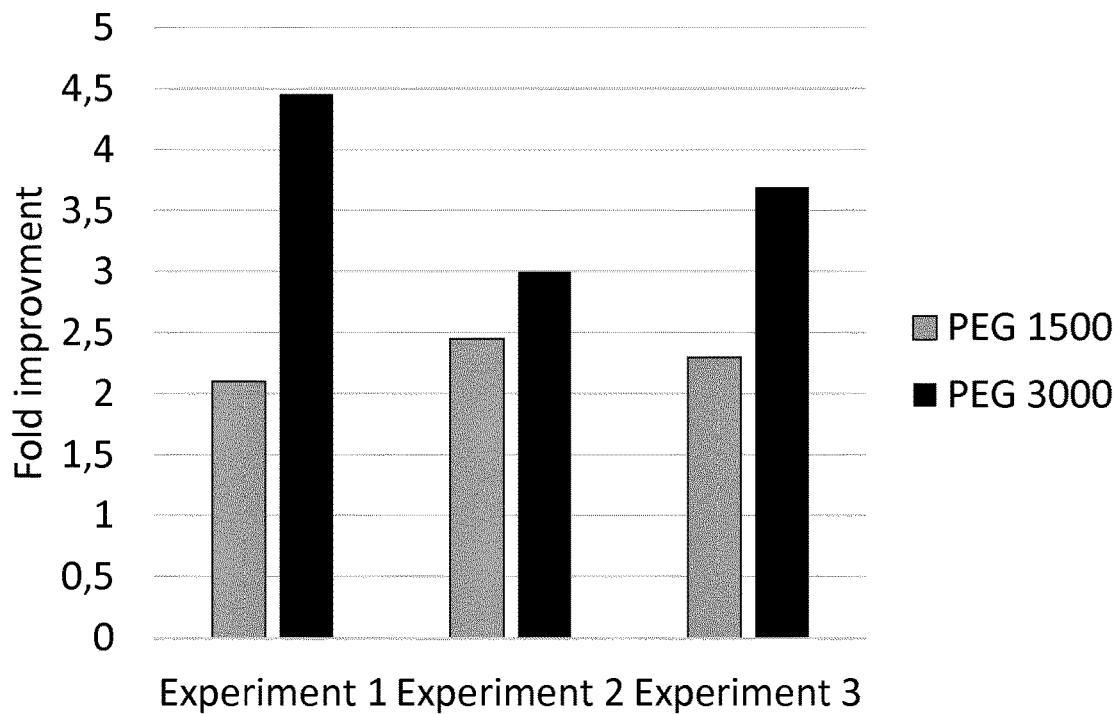
FIG. 15 is a bar diagram showing the Purification-Fold (A) and Purification-Yield (B) values for PEG 1500 and PEG 3000 obtained from three independent experiments. The mean value±standard deviation are shown in Table 5 (Example 2).
Figure 15:
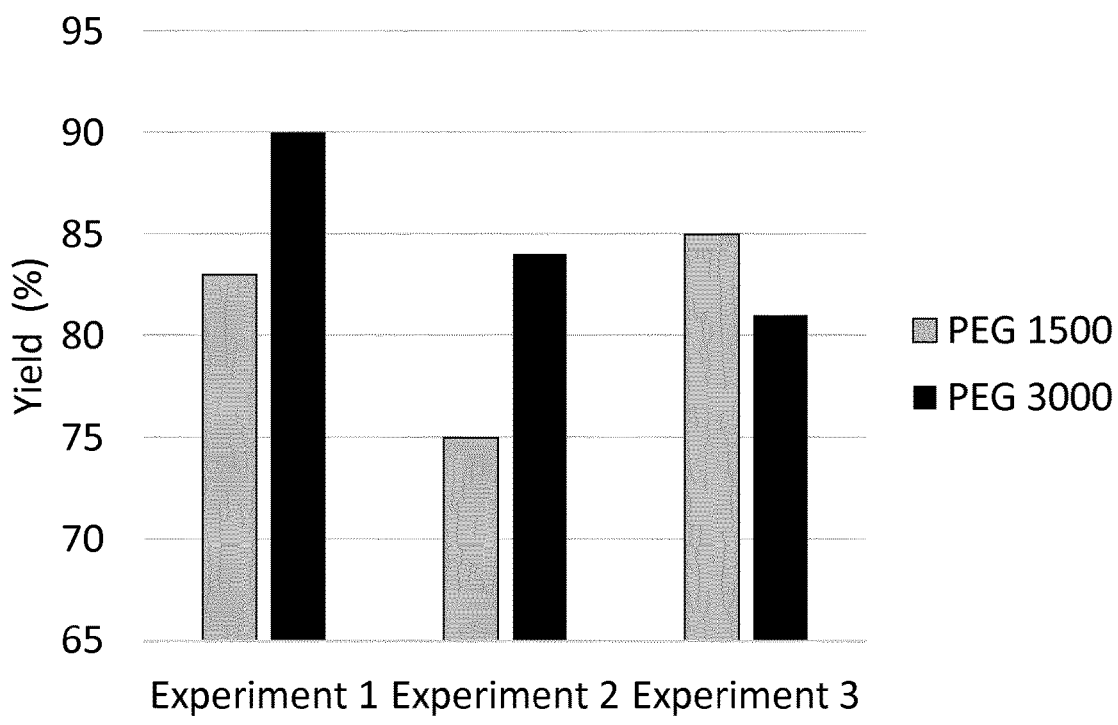

The purification-fold and purification-yield for the Pi phase were calculated for each experiment. The results are shown in Table 5 and FIG. 15.

TABLE 5

Purification-Fold and Purification-Yield (%) values for PEG 1500 and PEG 3000 expressed as mean ± standard deviation of 3 independent experiments

| PEG | Purification-Fold | Purification-Yield (%) |
|---|---|---|
| PEG 1500 | 2.3 ± 0.2 | 81 ± 5 |
| PEG 3000 | 3.7 ± 0.7 | 85 ± 4.5 |

2.3. ATPS Scale-Up Experiment

The reproducibility of the optimized ATPS conditions was tested in a final preparation of 100 g. The conditions which had shown the best purification-fold and purification-yield improvements were the following:
PEG 1500: 12% w/w PEG, 20% w/w Pi supplemented with 10% w/w NaCl (final concentrations)
PEG 3000: 12% w/w PEG, 20% w/w Pi supplemented with 3.5% w/w NaCl (final concentrations)

Procedure:

1 g of freeze-dried *T. chuii* cells were lysed in 10 mL 220 mM Pi, pH 7.8. The cells were lysed by applying ultrasounds as follows: 10×40 s in ice, 40% amplitude using the small tip. Subsequently, the cells were centrifuged for 20 min at 16,000×g and the supernatant was used for setting up the ATPS. The final ATPS consisted of 24 g PEG, 50 g Pi, 10 g cell extract and 16 g ddH$_2$O. The mixtures were rotated for 1 h at room temperature, followed by mild centrifugation at 1,500 rpm for 10 min in order to accelerate the phase separation.

Figure 16:
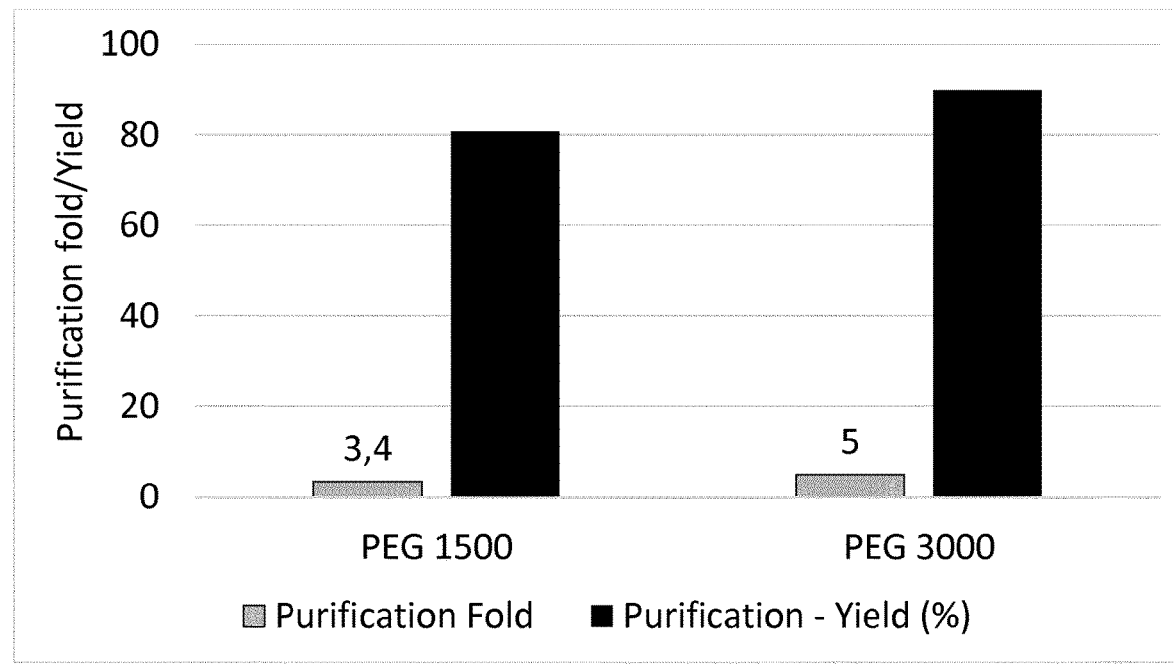
FIG. 16 is a bar diagram showing the performance of ATPS scale-up experiment (100 g).

SOD activity of the Pi phase was determined employing the cytochrome c assay (Example 1); the total protein concentration was measured by the Bradford method (cited supra). The purification-fold and purification-yield were calculated. The results are shown in FIG. 16. As it is shown in said FIG. 16, again sufficient purification (3-5 fold) with high recovery (>80%) was achieved for SOD at the bottom phosphate phase.

2.4. Heat Treatment of Crude Extract and Pi Phase Aiming at the Improvement of the Specific Activity The purpose of this experiment was to investigate whether a thermal treatment of the crude extract fraction, before application to ATPS, could improve SOD specific activity.

Figure 17:
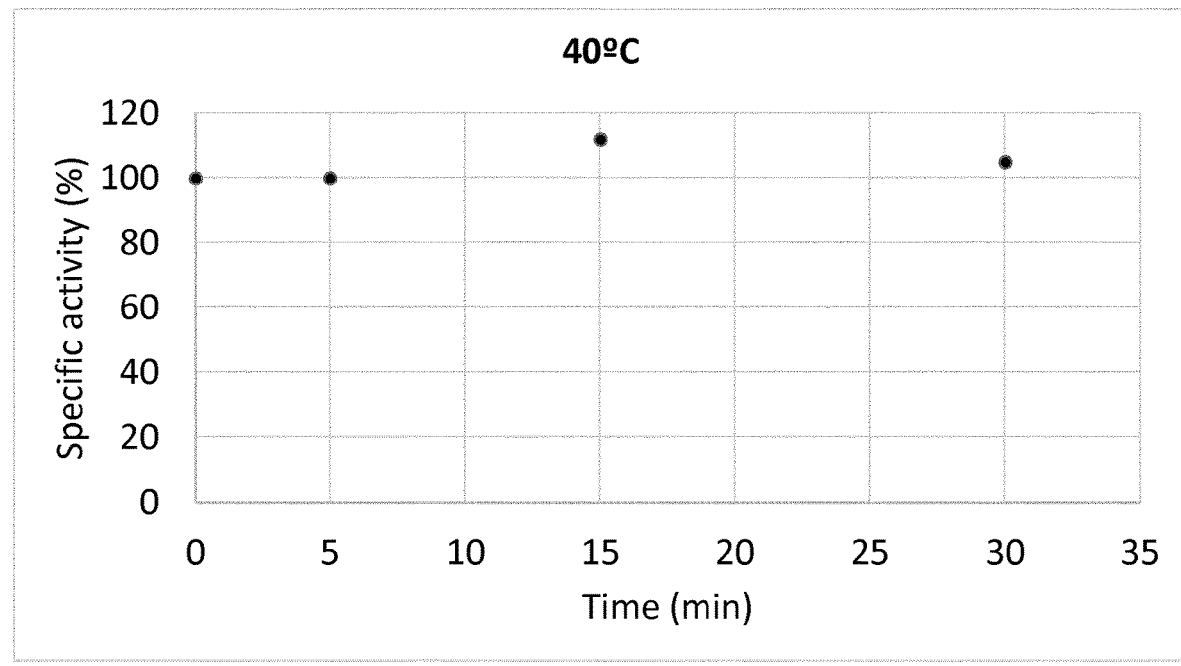
FIG. 17 is a graph showing the specific SOD activity (%) as a function of time of the crude extract after thermal treatment at 40° C.
Figure 18:
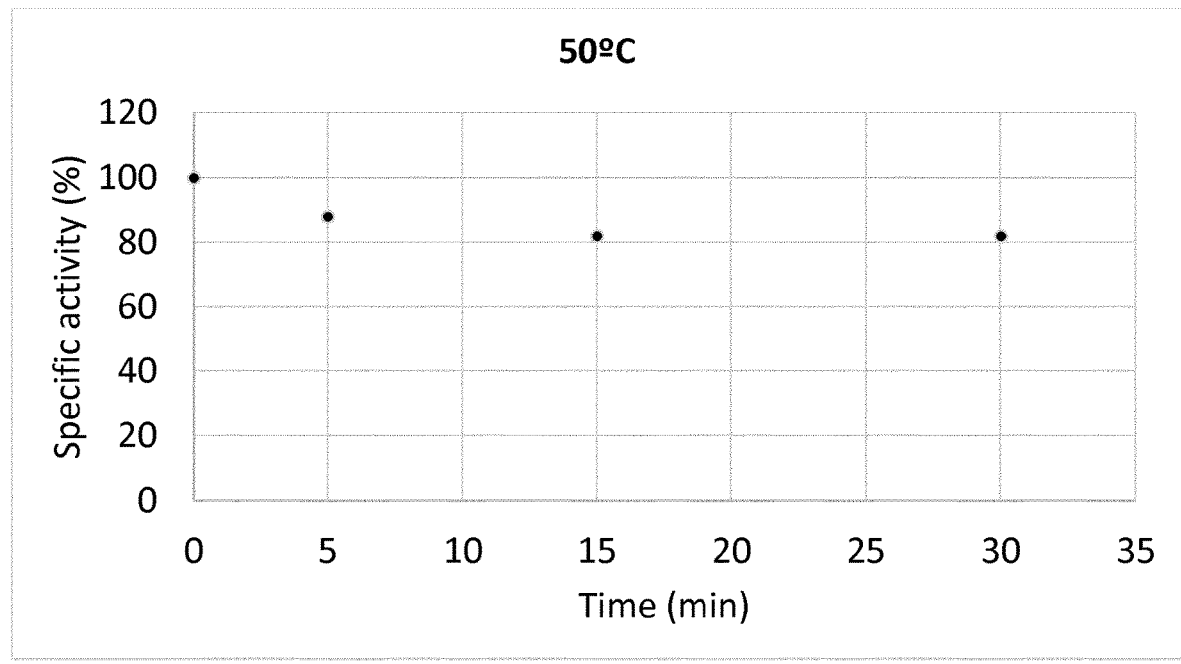
FIG. 18 is a graph showing the specific SOD activity (%) as a function of time of the crude extract after thermal treatment at 50° C.

For the heat treatment of the crude extract, 0.1 g *T. chuii* cells were lysed as described previously and centrifuged at 16.000×g for 20 minutes; subsequently, the supernatant crude extract was subjected to thermal incubation at 2 different temperatures: 40° C. and 50° C. At different time points aliquots were removed and total SOD activity was determined employing the cytochrome c assay. Additionally, the total protein concentration was determined by the Bradford method (cited supra). The results are shown in FIGS. 17 and 18.

For the heat treatment of the Pi phase after ATPS, the same hypothesis was tested using the Pi phase of the two optimized ATPS conditions (PEG 1500 and PEG 3000).

Figure 19:
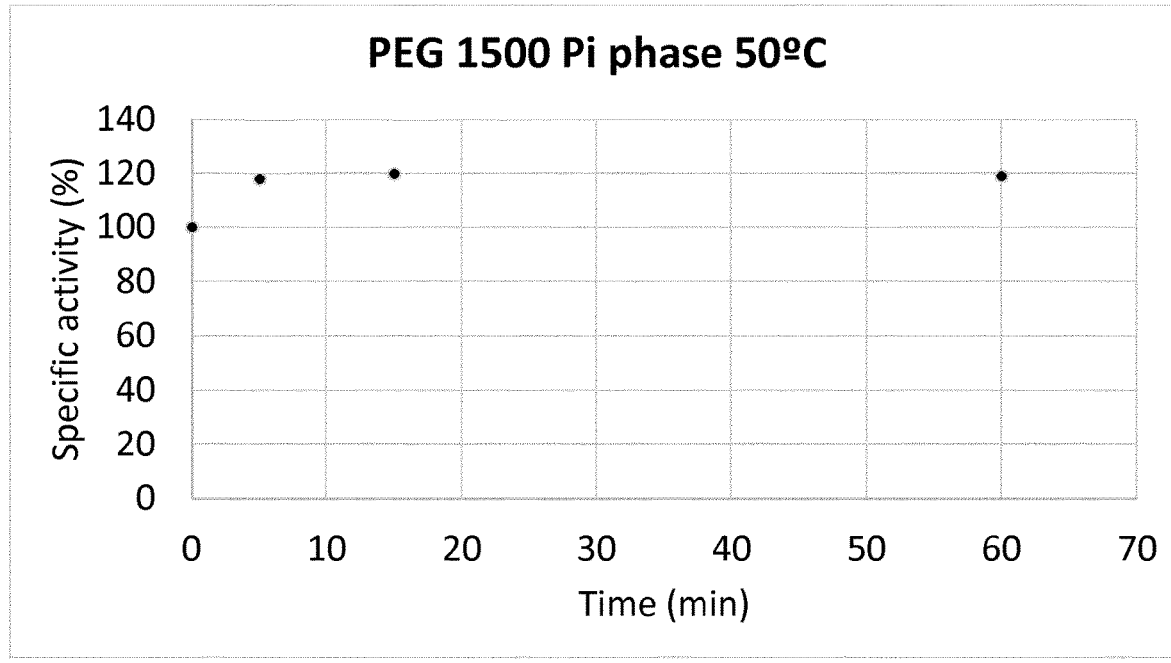
FIG. 19 is a graph showing the specific SOD activity (%) as a function of time of the PEG 1500 Pi phase after thermal treatment at 50° C.
Figure 20:
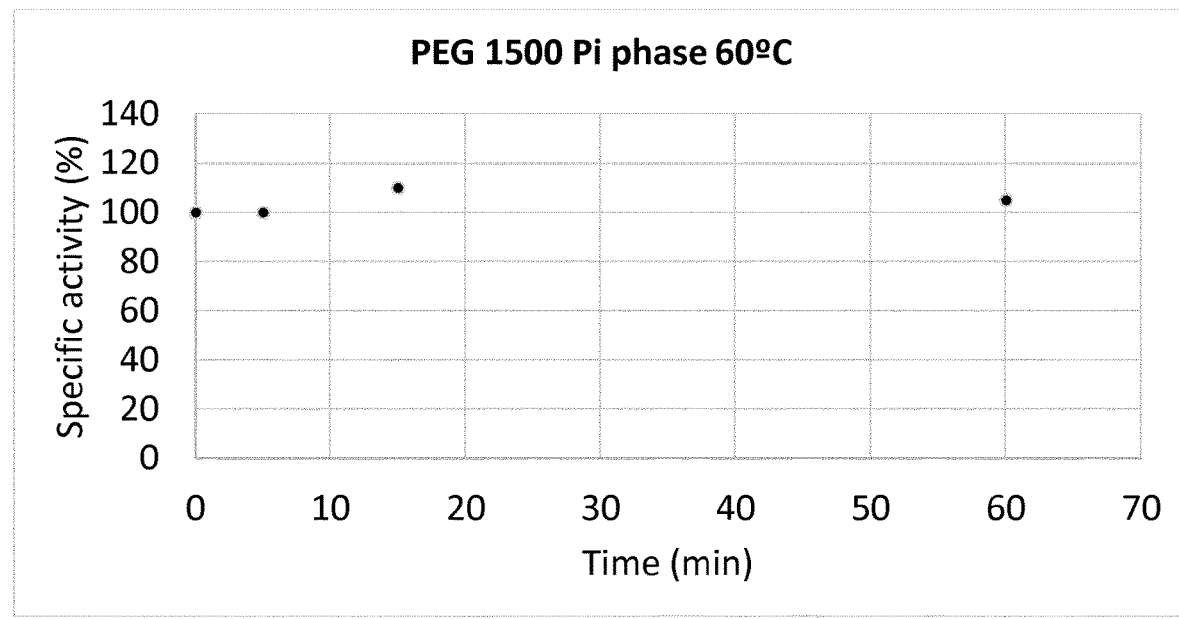
FIG. 20 is a graph showing the specific SOD activity (%) as a function of time of the PEG 1500 Pi phase after thermal treatment at 60° C.
Figure 21:
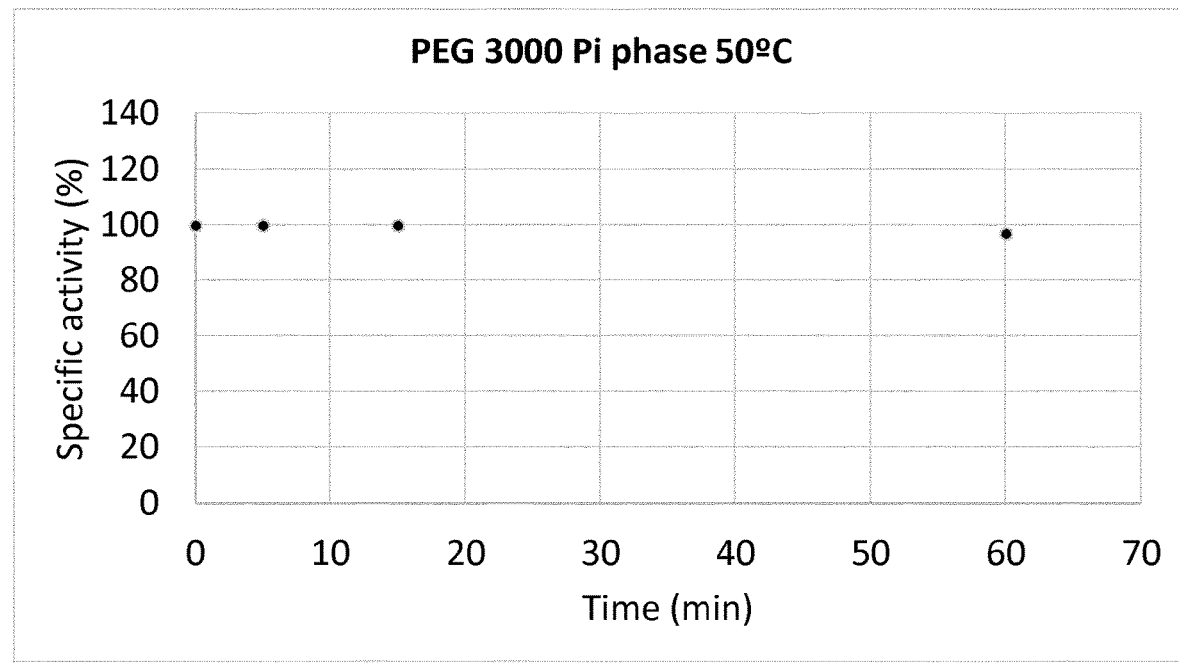
FIG. 21 is a graph showing the specific SOD activity (%) as a function of time of the PEG 3000 Pi phase after thermal treatment at 50° C.
Figure 22:
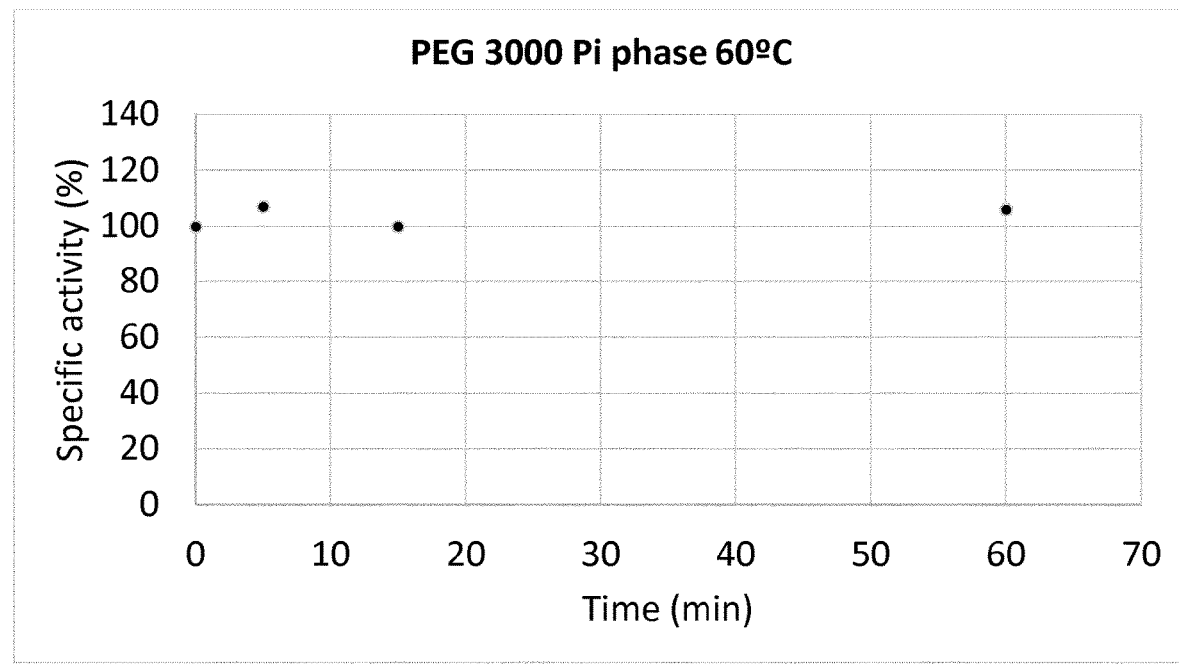
FIG. 22 is a graph showing the specific SOD activity (%) as a function of time of the PEG 3000 Pi phase after thermal treatment at 60° C.

Following ATPS, the Pi phase was subjected to heat treatment at 50° C. and 60° C. The results for PEG 1500 Pi phase are shown in FIGS. 19 and 20. The results for PEG 3000 Pi phase are shown in FIGS. 21 and 22. These results show that the SOD/phosphate phase exhibits high thermostability at 50° C. and 60° C.

2.5. Phase Formation in ATPS Without Centrifugation

The possibility of formation of the two phases (PEG and Pi), as well as the interface between them, without centrifugation, using the two optimized ATPS conditions was investigated. This would facilitate large scale purification and lower the cost of the process. The conditions were the following:

PEG 1500: 12% w/w PEG, 20% w/w Pi supplemented with 10% w/w NaCl (final concentrations)
PEG 3000: 12% w/w PEG, 20% w/w Pi supplemented with 3.5% w/w NaCl (final concentrations)

Figure 23:
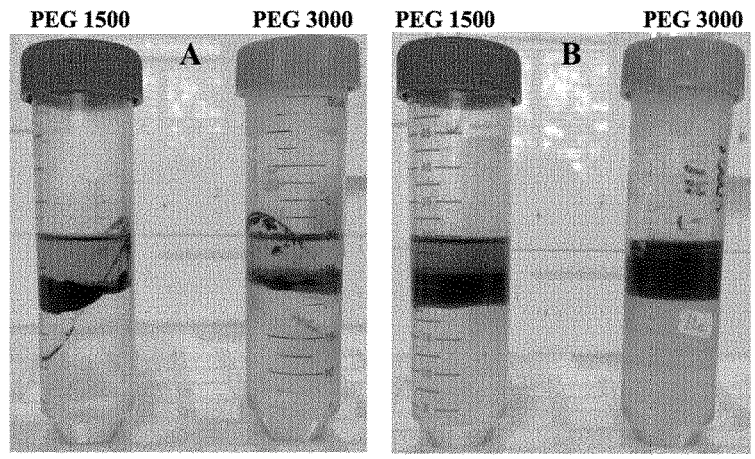
FIG. 23 is a photo showing the phase formation of the optimized ATPS conditions after (A) centrifugation 10 minutes at 1,600×g and (B) 12 h upon equilibrium.
Figure 24:
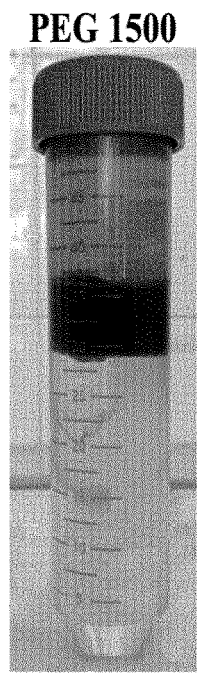
FIG. 24 is a photo showing the phase formation of the optimized PEG 1500 ATPS conditions 12 h upon equilibrium at final weight of about 65 g.

The mixtures (about 40 g final weight) were left at room temperature to equilibrate after rotation for 1 h. Phase separation was observed only in case of PEG 1500 after overnight incubation. The result was reproduced using a 65 g system. Pictures of the two systems are shown in FIGS. 23 and 24. For comparison reasons, the centrifuged versions of the samples are included.

EXAMPLE 3

In Vitro Assessment of the Protective Effect of *T. chuii* Cell Free Extract Against $H_2O_2$ in NHDF Cells Materials & Methods Extract: *T. chuii* Cell Free Extract (Obtained as Described in Example 1)
In Vitro Toxicity Assay Primary Human Dermal Fibroblasts (NHDF) isolated from normal human adult skin were obtained from Lonza Clonetics™ (Lonza Walkersville, USA). Cells were cultured at 37° C. in a 5% $CO_2$ atmosphere, using the recommended media FGM™-2 BulletKit™ containing 2% serum. For the assessment of the protective effect of *T. chuii* cell free extract against $H_2O_2$ elicited oxidative damage, NHDF cells were pre-incubated for 48 h in the growth medium containing *T. chuii* cell free extract (obtained as described in Example 1) at a final concentration of 300 μg/ml (w/v). Prior to $H_2O_2$ treatment the cells were washed twice with 1×PBS (137 mM NaCl, 2.7 mM KCl, 10 mM $Na_2HPO_4$, 2 mM $KH_2PO_4$), in order to prevent direct extracellular interactions between the extract compounds and $H_2O_2$. Finally, $H_2O_2$ was added in the medium at a final concentration of 0.5 nM, and the cells were incubated at 37° C. for 3 hours. Cytotoxicity was assessed by determining the ATP levels using the ATP Vialight plus Kit (Lonza Walkersville, USA) according to the manufacturer standard protocol.

Results

Figure 25:
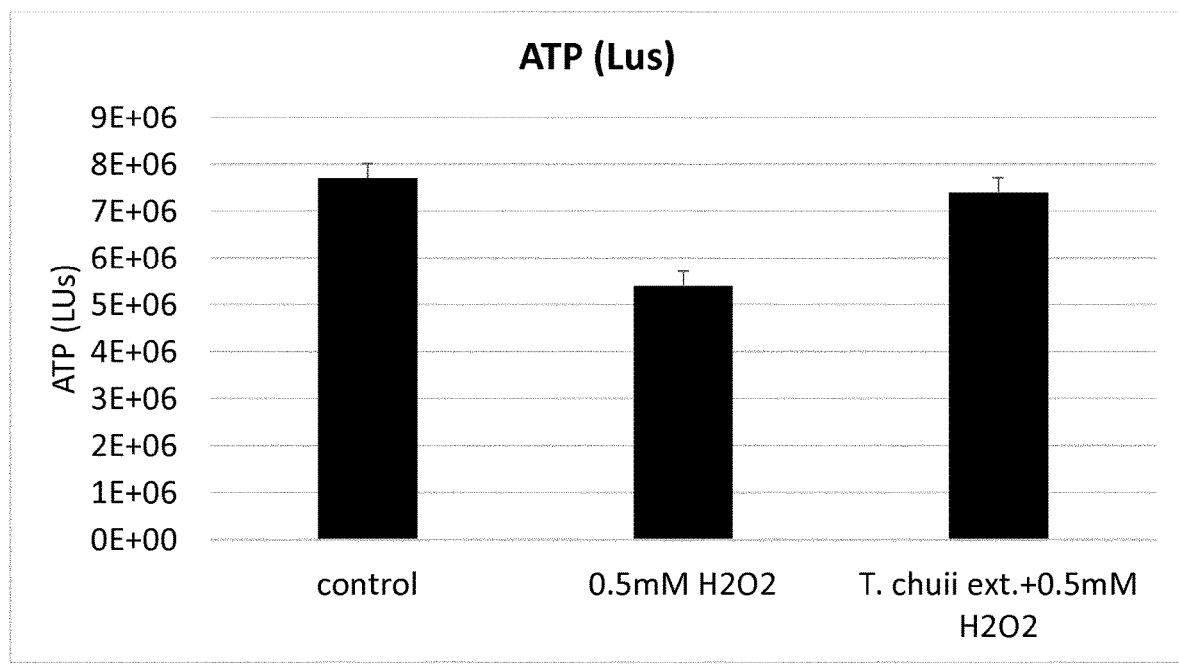
FIG. 25 is a bar diagram showing the results of the in vitro protection assay of *T. chuii* cell free extract against cell toxicity caused by $H_2O_2$ on cultured NHDF cells. Cell viability was estimated by ATP content measured as luciferase units (LUs) (Example 3).

The protective effect of the *T. chuii* cell free extract against oxidative damage elicited by $H_2O_2$ was studied using in vitro toxicity assays on isolated primary Human Dermal Fibroblasts (NHDF). NHDF cells were pre-incubated for 48 h in the growth medium containing *T. chuii* and oxidative stress was elicited by the addition of 0.5 nM $H_2O_2$. For estimating cytotoxicity, NHDF cells were also treated with $H_2O_2$ without the previous addition of the *T. chuii* cell free extract, while untreated NHDF cells were used as a control. Cytotoxicity was assessed by determining the cellular ATP levels (FIG. 25). This analysis revealed that the pre-treatment of the NHDF cells with the *T. chuii* cell free extract resulted in the significant protection of cell viability when compared to the cells exposed to $H_2O_2$ without the previous addition of the extract. Therefore, the *T. chuii* cell free extract effectively protects human primary skin fibroblast against oxidative damage caused by $H_2O_2$.

The invention claimed is:

1. A method for obtaining a biomass of a microalga of the species *Tetraselmis chuii* enriched in superoxide dismutase (SOD), the method comprises:
    culturing said microalga under abiotic stress,
    wherein said abiotic stress is selected from the group consisting of a redox potential of at least 100 mV in the culture medium, a temperature greater than 28° C. in the culture medium, nitrogen starvation at a nitrate concentration in the culture media of less than 5 μM and a salinity greater than 41 practical salinity units (PSU) in the culture medium.

2. A biomass of a microalga of the species *Tetraselmis chuii* (*T. chuii*) enriched in superoxide dismutase (SOD) obtained by the method according to claim 1, wherein the biomass has a SOD activity higher than 180 IU/mg of soluble protein.

3. The biomass according to claim 2, wherein the biomass has been dehydrated or brine-treated.

4. The biomass of a microalga of the species *Tetraselmis chuii* (*T. chuii*) enriched in superoxide dismutase (SOD) according to claim 2,
    wherein the SOD is stabilized with a brine,
    wherein the brine comprises
        between 10 and 18 g/L total sulphur (S),
        between 40 and 55 g/L sulphate ($SO_4^{2-}$),
        between 60 and 1,500 mg/L calcium ($Ca^{2+}$),
        between 52 and 70 g/L magnesium ($Mg^{2+}$),
        and between 15 and 20 g/L potassium ($K^+$),
        between 9 and 20 g/L sodium ($Na^+$), and
        between 115 and 180 g/L chloride ($Cl^-$) and
    wherein the brine has a density between 1.25 and 1.30 g/ml at 20° C.

5. The biomass according to claim 2 obtained by a method comprising culturing the microalga under abiotic stress, wherein said abiotic stress is a redox potential of at least 100 mV in the culture medium.

6. The biomass according to claim 2 obtained by a method comprising culturing the microalga under abiotic stress, wherein said abiotic stress is a temperature greater than 28° C. in the culture medium.

7. The biomass according to claim 2 obtained by a method comprising culturing the microalga under abiotic stress, wherein said abiotic stress is nitrogen starvation at a nitrate concentration in the culture media of less than 5 μM.

8. The biomass according to claim 2 obtained by a method comprising culturing the microalga under abiotic stress, wherein said abiotic stress is a salinity greater than 41 practical salinity units (PSU) In the culture medium.

9. The biomass of a microalga of the species *Tetraselmis chuii* (*T. chuii*) enriched in superoxide dismutase (SOD) according to claim 2, having a SOD activity of equal to or higher than 250 IU/mg of soluble protein.

10. The biomass of a microalga of the species *Tetraselmis chuii* (*T. chuii*) enriched in superoxide dismutase (SOD) according to claim 9, obtained by culturing said microalga under a redox potential of at least 100 mV in the culture medium.

11. A foodstuff or a pharmaceutical composition comprising the biomass of a microalga of the species *T. chuii* enriched in SOD according to claim 2.

12. The foodstuff or a pharmaceutical composition according to claim 11, wherein the biomass of a microalga of the species *T. chuii* enriched in SOD has been dehydrated or brine-treated.

13. A method for the stabilization of SOD from the biomass of a microalga of the species *T. chuii* enriched in SOD according to claim 2, the method comprising:
   contacting said biomass with a brine
   wherein said brine comprises:
      between 10 and 18 g/L total sulphur (S),
      between 40 and 55 g/L sulphate ($SO_4^{2-}$),
      between 60 and 1,500 mg/L calcium ($Ca^{2+}$),
      between 52 and 70 g/L magnesium ($Mg^{2+}$),
      between 15 and 20 g/L potassium ($K^+$),
      between 9 and 20 g/L potassium ($Na^+$),
      between 115 and 180 g/L chloride ($Cl^-$) and
   wherein the brine has a density between 1.25 and 1.30 g/ml at 20° C. as a stabiliser of SOD, wherein said biomass is the biomass of a microalga.

* * * * *